US010246560B2

(12) United States Patent
Lu et al.

(10) Patent No.: US 10,246,560 B2
(45) Date of Patent: Apr. 2, 2019

(54) PLGA-MODIFIED POLYETHYLENIMINE SELF-ASSEMBLY NANOTECHNOLOGY FOR NUCLEIC ACID AND DRUG DELIVERY

(71) Applicant: Baylor College of Medicine, Houston, TX (US)

(72) Inventors: Jian-Ming Lu, Pearland, TX (US); Qizhi Yao, Houston, TX (US); Changyi Chen, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 0 days.

(21) Appl. No.: 14/911,399

(22) PCT Filed: Aug. 13, 2014

(86) PCT No.: PCT/US2014/050930
§ 371 (c)(1),
(2) Date: Feb. 10, 2016

(87) PCT Pub. No.: WO2015/023775
PCT Pub. Date: Feb. 19, 2015

(65) Prior Publication Data
US 2016/0184443 A1 Jun. 30, 2016

Related U.S. Application Data

(60) Provisional application No. 61/865,189, filed on Aug. 13, 2013.

(51) Int. Cl.
| *A61K 47/00* | (2006.01) |
| *C08G 81/00* | (2006.01) |
| *C12N 15/88* | (2006.01) |
| *A61K 48/00* | (2006.01) |
| *C08G 81/02* | (2006.01) |
| *C08G 63/91* | (2006.01) |
| *C08G 63/685* | (2006.01) |
| *C08G 73/02* | (2006.01) |
| *A61K 47/60* | (2017.01) |
| *A61K 47/59* | (2017.01) |
| *A61K 47/69* | (2017.01) |

(52) U.S. Cl.
CPC ............ *C08G 81/00* (2013.01); *A61K 47/59* (2017.08); *A61K 47/593* (2017.08); *A61K 47/60* (2017.08); *A61K 47/6929* (2017.08); *A61K 47/6935* (2017.08); *A61K 47/6937* (2017.08); *A61K 48/005* (2013.01); *A61K 48/0041* (2013.01); *C08G 63/6852* (2013.01); *C08G 63/912* (2013.01); *C08G 73/0206* (2013.01); *C08G 81/027* (2013.01); *C12N 15/88* (2013.01); *C12N 2310/14* (2013.01); *C12N 2310/141* (2013.01); *C12N 2320/32* (2013.01)

(58) Field of Classification Search
None
See application file for complete search history.

(56) References Cited

U.S. PATENT DOCUMENTS

| 2003/0009004 A1* | 1/2003 | Nam .................... A61K 9/1075 528/272 |
| 2011/0250225 A1 | 10/2011 | Fotin-Mleczek et al. |
| 2011/0312877 A1 | 12/2011 | Berninger et al. |
| 2012/0114759 A1 | 5/2012 | Green et al. |
| 2012/0128782 A1 | 5/2012 | Green et al. |

FOREIGN PATENT DOCUMENTS

| CN | 102123733 A | 7/2011 |
| CN | 102316858 A | 1/2012 |
| WO | 2012109363 A2 | 8/2012 |

OTHER PUBLICATIONS

Sutton et al. Poly(D,L-lactide-co-glycolide)/Poly(ethylenimine) Blend Matrix System for pH Sensitive Drug Delivery. Journal of Applied Polymer Science, 2006. 100:89-96.*
Shau et al. A One-Step Process in Preparation of Cationic Nanoparticles with Poly(lactide-co-glycolide)-Containing Polyethylenimine Gives Efficient Gene Delivery. European Journal of Pharmaceutical Sciences, 2012. 46:522-529, available online Apr. 13, 2012.*
Lee et al. Polyethylenimine-g-Poly(lactic-co-glycolic acid) as Non-Toxic Micelle-Type Carrier for Gene Delivery. Macromolecular Research, 2011. 19(7):688-693.*
Oster et al. Cationic Microparticles Consisting of Poly(lactide-co-glycolide) and Polyethylenimine as Carrier Systems for Parental DNA Vaccination. Journal of Controlled Release, 2005.*
Hoskins et al. A Review On Comb-Shaped Amphiphilic Polymers for Hydrophobic Drug Solubilization. Therapeutic Delivery, 2012:3(1): 59-79.*
Aravindan et al. Effect of Acyl Chain Length on Transfection Efficiency and Toxicity of Polyethylenimine. International Journal of Pharmaceutics. 2009. 378:201-210.*

(Continued)

*Primary Examiner* — Christopher M Babic
*Assistant Examiner* — Kimberly A. Aron
(74) *Attorney, Agent, or Firm* — Norton Rose Fulbright US LLP

(57) ABSTRACT

Embodiments of the invention concern copolymers and nanoparticles for use as delivery agents for one or more agents for therapy for a medical condition of humans and animals. Some of embodiments of the invention provide new reagents for biomedical research in cell culture, animal models and plants, for example. The copolymers comprise PLGA and PEI and, in some embodiments, also comprise 1-(3-aminopropyl)-4-methylpiperazine (APMP), Fc binding peptide and/or antibody. In certain embodiments, APMP-PLGA-PEI, Fc binding peptide/antibody-PLGA-PEI or Fc binding peptide/antibody-AP-MP-PLGA-PEI nanoparticles comprising one or more therapeutic agents are delivered to an individual in need thereof or used for biomedical research in cell cultures, animal models and plants.

4 Claims, 25 Drawing Sheets
Specification includes a Sequence Listing.

(56) References Cited

OTHER PUBLICATIONS

Bhatia, S. "Nanoparticles Types, Classification, Characterization, Fabrication Methods and Drug Delivery Applications" in Natural Polymer Drug Delivery Systems, 2016. Springer International Publishing, Switzerland. pp. 33-93.*

Nam et at., "New micelle-like polymer aggregates made from PEI-PLGA diblock copolymers: micellar characteristics and cellular uptake", Biomaterials, May 1, 2003 (May 1, 2003), vol. 24, No. 12, pp. 2053-2059.

Li et at., "(3-aminopropyl}-4-methylpiperazine end-capped poly(1,4-butanediol diacrylate~-amino-1-butanol)-based multilayer films for gene delivery," ACS Appl Mater Interfaces, Jun. 24, 2013 (Jun. 24, 2013), vol. 5, No. 13, pp. 5947-5953.

Menon, et al. Effects of surfactants on the properties of PLGA nanoparticles. Journal of Biomedical Materials Research—Part A, 2012, 100 A(8), 1998-2005.

* cited by examiner

PLGA-PEI polymer (0.6/1 w/w)
(1 PEI and 109 LGA single units)

NP 35 nm (3.5 μg PLGA-PEI/10 μg DNA)
(1 plasmid and 313 polymers)

NP 100 nm (25 μg PLGA-PEI/10 μg DNA)
(15 plasmids and 3345 polymers)

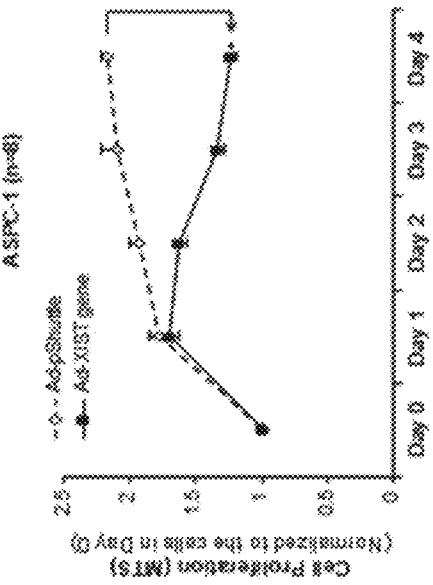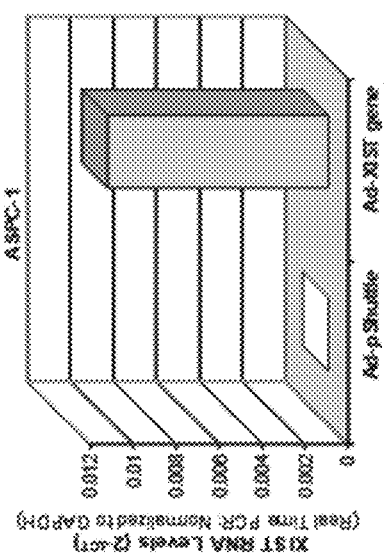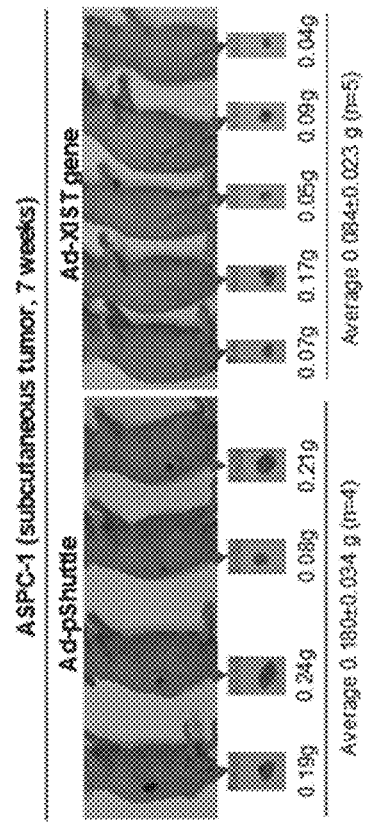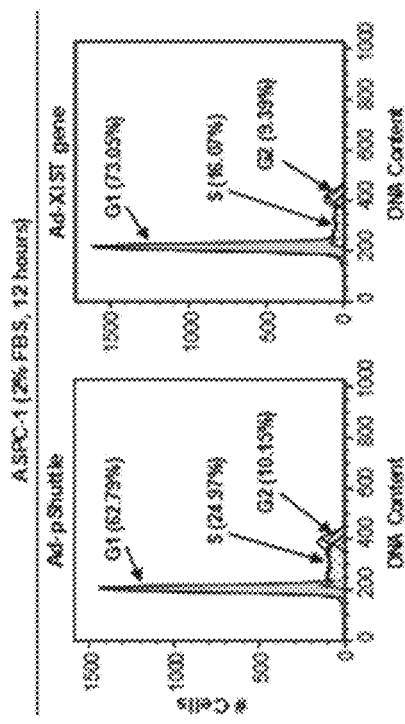
FIG. 14A
FIG. 14B
FIG. 14C
FIG. 14D

SEQUENCE LISTING

```
<160> NUMBER OF SEQ ID NOS: 3

<210> SEQ ID NO 1
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 1

Cys Gly Gly Gly Gly Asp Cys Ala Trp His Leu Gly Glu Leu Val Trp
1               5                   10                  15

Cys Thr Gly Gly Gly Gly Cys
            20

<210> SEQ ID NO 2
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 2

Asp Cys Ala Trp His Leu Gly Glu Leu Val Trp Cys Thr
1               5                   10

<210> SEQ ID NO 3
<211> LENGTH: 36
<212> TYPE: PRT
<213> ORGANISM: Artificial Sequence
<220> FEATURE:
<223> OTHER INFORMATION: Synthetic Peptide

<400> SEQUENCE: 3

Cys Gly Gly Gly Gly Asp Cys Ala Trp His Leu Gly Glu Leu Val Trp
1               5                   10                  15

Cys Thr Asp Cys Ala Trp His Leu Gly Glu Leu Val Trp Cys Thr Gly
            20                  25                  30

Gly Gly Gly Cys
            35
```

PLGA-MODIFIED POLYETHYLENIMINE SELF-ASSEMBLY NANOTECHNOLOGY FOR NUCLEIC ACID AND DRUG DELIVERY

This application is a national phase application under 35 U.S.C. § 371 that claims priority to International Application No. PCT/US2014/050930 filed Aug. 13, 2014, which claims priority to U.S. Provisional Patent Application Ser. No. 61/865,189, filed Aug. 13, 2013, all of which are incorporated by reference herein in their entirety.

TECHNICAL FIELD

The field of the present invention includes at least the fields of medicine, nanotechnology, biology, cell biology and/or molecular biology.

BACKGROUND

Gene and drug delivery systems are a very active field of scientific research and invention because of the significant needs for clinical applications of diagnosis and treatment and scientific research in vitro and in vivo as well as its limitations of currently available technologies. For example, poly(lactide-co-glycolide) (PLGA)-based nanoparticle has been developed for drug delivery; however, it has a very low efficiency to load and deliver nucleic acids such as DNA and RNA because of its chemical nature. Liposome and polyethylenimine (PEI) have been developed for delivering nucleic acid such as DNA and RNA in vitro and in vivo. However, efficiency of these delivery systems is limited; toxicity is also high; and preparation procedures are complicated. Currently, there are no delivery systems that have high efficacy and low toxicity in clinical applications. The present invention satisfies a long-felt need in the art for an efficient, low toxicity system to deliver at least one agent to an individual.

SUMMARY

Embodiments of the invention concern a useful delivery system for delivering to an individual at least one of any type of agent, including at least nucleic acids, proteins, small molecules, and/or drugs of any kind. Some embodiments of the invention concern compositions and methods utilizing PLGA-modified polyethylenimine nanotechnology. In certain aspects, the invention concerns PLGA-PEI conjugates and methods of use and methods of making. Embodiments encompass the chemical conjugation of PEI and PLGA, in at least some cases, in a particular PLGA to PEI ratio. Such embodiments can render the self-assembly nanoparticle formation with one or more agents. In specific embodiments, an agent is DNA and/or RNA and the complexes have a high DNA and/or RNA loading efficiency, high DNA and/or RNA transfection efficacy, and low cytotoxicity.

Certain embodiments concern the chemical reaction between PLGA and PEI and resultant compositions therefrom. Provided herein are examples of conditions, including exemplary conditions, of PLGA-modified PEI self-assembly nanoparticle formation with DNA loading, for example. Embodiments of the invention provide efficient DNA delivery without toxicity in vitro and in vivo.

In particular embodiments of the invention, there is a composition comprising APMP (APMP: 1-(3-aminopropyl)-4-methylpiperazine)-PLGA-PEI as a new material with new applications. Some embodiments include primary amine quantitation in PLGA-PEI nanoparticles, allowing a new approach to control PLGA fragment size and contents linked to PEI for particular DNA (as an example) loading and particle size design.

Embodiments of the invention include a formulation of PLGA-PEI/nucleic acid nanoparticle: self-assembly of nanoparticle formation from PLGA-PEI and nucleic acid (DNA) that utilizes certain preparation steps, no organic solvents or special medium, is more effective, and/or is less toxic.

Embodiments of the invention provide a new PLGA-PEI material having a different reaction time and condition, new structure, new composition, new properties and/or new functions/applications.

Embodiments of the invention provide a new mechanism of PLGA-PEI/DNA nanoparticle formation, including aspects of chemical composition, DNA interaction, particle formation, and nanoparticle imaging. PLGA-PEI or APMP-PLGA-PEI can load a wide range of DNA contents for cellular delivery and transfect cells more efficiently with less toxicity than other delivery agents including lipofectamine 2000 and PEI, for example.

Embodiments of the invention provide a useful combination of gene therapy and chemotherapy. PLGA-PEI or APMP-PLGA-PEI is useful to deliver therapeutic genes and chemotherapeutic drugs together, for example. In certain cases, one or more specific antibodies can be linked to PEG-PLGA-PEI or APMP-PLGA-PEI for targeting specific cell types. This technology is particular useful for the targeted therapy to cancers or other diseases. Antibodies may be linked to complexes of the disclosure by conjugation, for example.

In some embodiments, the nanoparticles of the present invention are employed with another therapeutic compound separate from the nanoparticle for treatment of the same indication in the individual. In particular cases, the nanoparticles and the therapeutic compound are delivered separately or together. When delivered together, they may or may not be in the same formulation, and they may or may not be delivered by the same route.

In embodiments, there is a copolymer composition comprising poly(lactic-co-glycolic acid) (PLGA) and polyethylenimine (PEI), wherein the w/w ratio of PLGA to PEI is 0.5:1, 1:1, 2:1, or 5:1.

In embodiments, there is a copolymer composition comprising PLGA and PEI, wherein the w/w ratio of PLGA to PEI is 0.5:1 and wherein about 70-130 lactide-co-glycolide units from PLGA are conjugated to a PEI molecule through an amide linkage.

In one embodiment, there is a copolymer composition comprising PLGA and PEI, wherein the primary amine concentration is about 40% to about 55%. The primary amine concentration may be about 45% to about 55%, about 45% to about 52%, or about 46% to about 52%. The primary amine concentration may be 45% to 55%, 45% to 52%, or 46% to 52%.

In a certain embodiment, there is a copolymer composition comprising PLGA, PEI, and another compound selected from the group consisting of 1-(3-aminopropyl)-4-methylpiperazine (APMP), 2-(3-aminopropylamino)ethanol, 2-methyl-1,5-diaminopentane, 1-(3-aminopropyl)pyrrolidine, 4-aminophenyl disulfide and cystamine.

In an embodiment, there is a copolymer composition comprising PLGA, PEI, APMP, and a linker, such as a polyethylene glycol (PEG) linker, including Maleimide-PEG-NHS, for example. In some cases, the linker is a PEG biolinker (Mal-PEG-NHS) that chemically conjugates to PLGA-PEI or APMP-PLGA-PEI polymer to produce Mal- PEG-PLGA-PEI or Mal-PEG-APMP-PLGA-PEI, respectively. In certain cases, Mal-PEG-PLGA-PEI or Mal-PEG-APMP-PLGA-PEI chemically conjugates to Fc binding peptide or antibody for specific delivery.

In some embodiments, certain compositions further comprise at least one therapeutic and/or diagnostic agent and the copolymer comprises the agent in a nanoparticle. In specific embodiments, the therapeutic and/or diagnostic agent is suitably formulated for an animal disease, as a research reagent, or both. The therapeutic agent may be suitably formulated for human cancer, AIDS, heart disease, stroke, diabetes, respiratory disease, kidney disease, bacterial infection, and/or viral infection. In specific embodiments, the agent is a nucleic acid, protein, peptide, small molecule, antigen, vaccine, or mixture thereof. In cases where the nucleic acid is DNA, the DNA may be double stranded, single stranded, or a mixture thereof; the DNA may be an oligonucleotide. In cases wherein the nucleic acid is RNA, the RNA may be double stranded, single stranded, or a mixture thereof. The RNA may abe siRNA, shRNA, miRNA, or a mixture thereof. In specific cases, a diagnostic agent is labeled, including by color and/or fluorescence. In specific embodiments, when the ratio of PLGA to PEI is 0.5:1 w/w, the nanoparticle is between 100 and 130 nm.

In some embodiments, there is a method of making a composition of the disclosure, comprising the steps of: mixing APMP-co-1,4-butanediol diacrylate and PEI to produce a APMP-PEI polymer; and mixing the APMP-PEI polymer with PLGA to form the APMP-PLGA-PEI copolymer composition. 1,4-butanediol diacrylate-co-1-(3-aminopropyl)-4-methylpiperazine. In specific cases, the APMP-co-1,4-butanediol diacrylate and PEI are mixed for at least 24 hours. The APMP-PEI polymer and PLGA may be mixed for at least 12, 18, or 24 hours. In specific embodiments, the method further comprises the step of mixing the copolymer composition with at least one therapeutic and/or diagnostic agent.

In an embodiment, there is a method of treating an individual for a medical condition, comprising the step of delivering to the individual a therapeutically effective amount of a composition of the disclosure to the individual. In specific embodiments, the composition is delivered more than once. The composition may be delivered by injection. The composition may be delivered intraperitoneally or intravenously. In some cases the method further comprises delivering to the individual a therapeutically effective amount of another compound for treatment of the medical condition. In certain aspects, a method further comprises the step of identifying the individual as being in need of the treatment for the medical condition. The medical condition may be cancer.

In embodiments of the disclosure, the methods and/or compositions are employed in vitro, ex vivo, or in vivo. In specific embodiments, the methods and/or compositions are utilized in an in vitro setting to deliver a particular composition to a specific location. For example, the composition(s) may be used in cleaning compositions to affect the presence of bacteria, viruses, protozoa, etc., in a specific location, such as on one or more surfaces of a hospital, school, and the like.

DESCRIPTION OF THE DRAWINGS

For a more complete understanding of the present invention, reference is now made to the following descriptions taken in conjunction with the accompanying drawings.

FIG. 1A illustrates an embodiment of a mechanism for the formation of PLGA-PEI (the exemplary 0.5:1 w/w) (FIG. 1A), APMP-PLGA-PEI (FIG. 1B) and Fc binding peptide-PEG-PLGA-PEI or Fc binding peptide-PEG-APMP-PLGA-PEI (FIG. 1C).

FIG. 3B shows particle size distribution of nanoparticles prepared with 25 μg PLGA-PEI and 15 μg primer (23 nucleotides, single strand).

FIG. 4A demonstrates DNA loading efficiency of PLGA-PEI and FIG. 4B illustrates DNA retention of the nanoparticles. FIG. 4C showed DNA loading efficiency of APMP-PLGA-PEI nanoparticles by the DNA retention assay.

FIG. 5A shows when the DNA is condensed with PLGA-PEI at nitrogen/phosphorus ratio (N/P) of 7.4, resulting in particles around 150-230 nm. FIG. 5B shows nanoparticle size with more PLGA-PEI and the resulting size is 100-150 nm as N/P increased to 12.2. FIG. 5C demonstrates that when the N/P is increased to 17.2, the size is down to around 50 nm. PLGA-PEI is a polymer that condenses the DNA effectively as well as controls the particle size.

FIG. 7A shows PLGA-PEI/green fluorescence protein (GFP) DNA complexes evaluated for transfection efficacy in PANC-1 cells (pancreatic cancer cell line) compared to PEI and Lipofectamine 2000 delivery systems. FIG. 7B shows testing of the transfection efficiency of APMP-PLGA-PEI/GFP DNA nanoparticles in PANC-1 cells compared with PLGA-PEI, PEI and Lipofectamine 2000 delivery systems. At the same condition, APMP-PLGA-PEI has better delivery efficiency than PLGA-PEI, PEI and Lipofectamine 2000 delivery systems. FIG. 7C shows that PLGA-PEI nanoparticles have much higher transfection rate than Lipofectamine 2000 in human umbilical vein endothelial cells (HUVEVs). Different types of cells have different transfection rates in response to different transfection reagents. HUVECs are considered as difficult-to-transfect cells. Thus, PLGA-PEI delivery system has significant advantages over other delivery systems such as Lipofectamine 2000.

FIG. 11A shows reduction of primary and metasta-sized tumors in the mice treated with PLGA-PEI/miR-198 and Gemcitabine (by fluorescence imaging analysis). FIG. 11B shows confirmation of reduced tumor size in mice treated with PLGA-PEI/miR-198 and Gemcitabine (by direct measurement of dissected tumors).

FIG. 12A. PLGA-PEI copolymer. Each branched PEI molecule (25 kDa) has about 214 primary amines, 159 secondary amines and 212 tertiary amines. While each PLGA molecule (12~16 kDa) has average of 215 (184 to 246) ester bonds. When the PLGA and PEI are reacted at a molar ratio of 1:1 (w/w of 0.5:1) in organic solvent THF; and a new product PLGA-PEI copolymer is formed. The resulted PEI weight content in the PLGA-PEI copolymer is 64%; and 51% primary amines of PEI are used in the PLGA-PEI copolymer, indicating the primary amines of PEI reacted with the ester bonds of PLGA. The PEI remains intact since PLGA has no force to break down the chain of PEI. It is estimated that in each PEI molecule, about 109 primary amines are used. Based on ester bonds, PEI content and primary amine percentage, it was conclude that PLGA molecules are fragmented to lactide-co-glycolide (LGA) single units by PEI; thus multiple LGA units are formed. Therefore, 1 PEI molecule is conjugated with 109 LGA single units. FIG. 12B. Small particle of PLGA-PEI/DNA. The molecular weight of PLGA-PEI copolymer is about 37 kDa; and 5 kbp plasmid DNA is about 3300 kDa. For the 35 µg PLGA-PEI/10 µg DNA NPs, 10 µg DNA has $1.82 \times 10^{12}$ DNA molecules; and 35 µg PLGA-PEI has $5.69 \times 10^{14}$ molecules. Thus, the molecular ratio of PLGA-PEI to DNA is 313. If 1 DNA molecule and 313 PLGA-PEI molecules forms a NP, its weight is $2.468 \times 10^{-17}$ g. Assuming the density of the NP is 1 g/cm3, its volume is thus $2.468 \times 10^{-17}$ cm3 (or 24680 nm3), corresponding a particle diameter of 36 nm. Therefore, for the NPs sizing about 36 nm, it might contain 1 plasmid DNA molecule. FIG. 12C. Large particle of PLGA-PEI/DNA. For the 25 µg PLGA-PEI/10 µg DNA NPs, the molecular ratio of PLGA-PEI copolymer to DNA is 223. By the same method, it is estimated that the volume of 1 DNA molecule and 223 PLGA-PEI copolymers is $1.918 \times 10^{-17}$ cm3 (or 19180 nm3). The size of these NPs is about 100 nm, corresponding to a volume of 294524 nm3. This particle may contain about 15 DNA molecules and 3345 PLGA-PEI copolymers.

FIG. 13A. Expression of XIST in surgical pancreatic cancer tissues and their surrounding non-cancer tissues from 8 female patients. FIG. 13B. Expression of XIST in 5 female pancreatic cancer cell lines (ASPC-1, BxPC-3, Panc03.27, HPAC and SU86.86) and 3 female control cells including HPDE immortalized human pancreatic ductal epithelial cells), HUVEC (human umbilical vein endothelial cells), and AoSMC (human aortic smooth muscle cells).

FIGS. 14A-14D demonstrate effects of forced expression of XIST (2.6 kb) on cell proliferation, cell cycle, and tumor growth of ASPC-1 cells. FIG. 14A. Forced expression of XIST in ASPC-1 cells by recombinant adenovirus gene delivery (real time PCR). FIG. 14B. MTS assay for cell proliferation. FIG. 14C. Cell cycle analysis (flow cytometry). FIG. 14D. Subcutaneous tumor xenograft in nude mice.

Figure 1A:
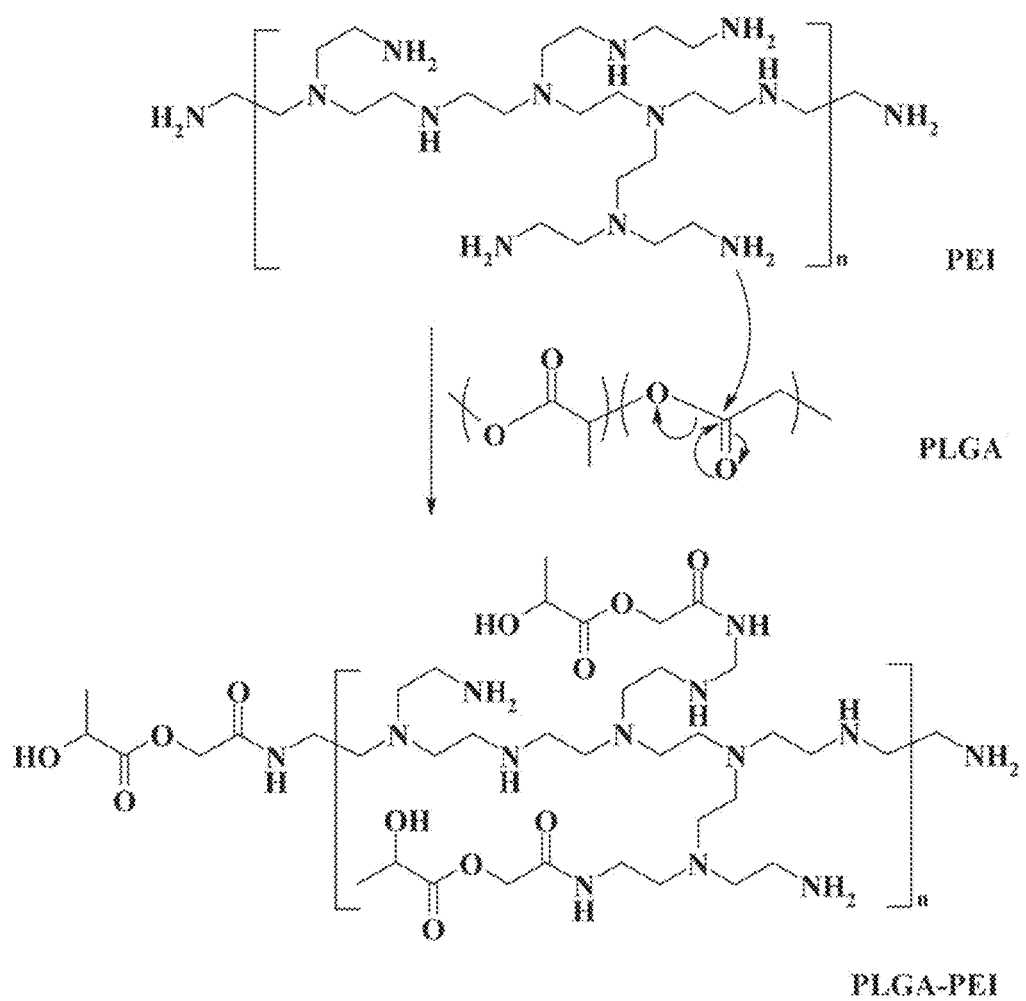
FIGS. 1A-1C.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

DETAILED DESCRIPTION

As used herein the specification, "a" or "an" may mean one or more. As used herein in the claim(s), when used in conjunction with the word "comprising", the words "a" or "an" may mean one or more than one. As used herein "another" may mean at least a second or more. In specific embodiments, aspects of the invention may "consist essentially of" or "consist of" one or more elements or steps of the invention, for example. Some embodiments of the invention may consist of or consist essentially of one or more elements, method steps, and/or methods of the invention. It is contemplated that any method or composition described herein can be implemented with respect to any other method or composition described herein.

I. General Embodiments

The present invention provides improvements over technology in at least the field of medicine including delivery of one or more therapeutic and/or diagnostic compositions. In specific embodiments, the system employs poly(lactide-co-glycolide) (PLGA), polyethylenimine (PEI), APMP (1-(3-aminopropyl)-4-methylpiperazine), and, may include another component. The other component, and in at least some cases, the component is an antibody. In particular embodiments, the component is a Fc-binding peptide.

In the art, poly(lactide-co-glycolide) (PLGA)-based nanoparticles have very low efficiency to load and deliver nucleic acids such as DNA and RNA because of the chemical nature of PLGA. Liposome and polyethylenimine (PEI) can be used to deliver nucleic acid such as DNA and RNA in vitro and in vivo. However, efficiency of this delivery system is limited, toxicity is high; and preparation procedures are complicated. Embodiments of the invention utilize at least both PLGA and PEI to achieve an efficient and useful system. Particular advantages of PLGA-modified PEI includes the following: 1) high efficiency of nucleic acids loading and delivering in vitro and in vivo; 2) a wide range of loading and delivering agents; 3) low toxicity; 4) self-assembly and easy procedure for preparation; 5). binding to specific antibody for specific delivery; and 6) broad applications in vitro and in vivo (animal and human use).

The method for the disclosed nanotechnology was optimized and characterized, including a chemical reaction and mechanism between PLGA and PEI, interaction between plasmid DNA and modified PLGA-PEI, and size and morphology of nanoparticles. DNA loading, transfection efficiency and cytotoxicity of the nanotechnology were characterized and carefully compared with available technologies, including lipofectamine 2000 and PEI in cell cultures. The nanotechnology shows better results in all of these critical measures as a DNA delivery system. In addition, the technology was studied in mouse models for DNA delivery and toxicity and compared with the PEI delivery system. The disclosed nanotechnology shows a higher delivery efficiency into major organs including at least liver, spleen and pancreas, and it has a much lower toxicity in mice compared with the PEI delivery system. More importantly, the inventors have conducted a study to use the technology to deliver an exemplary therapeutic miRNA construct in a nude mouse model of human pancreatic cancer. Both intraperitoneal and tail vein delivery routes of the nanotechnology with therapeutic miR-198 significantly inhibited tumor growth in the mice.

In specific embodiments, the subject matter of the disclosure provides a one-step preparation of PLGA-PEI polymers, including those which are easy for industry production, for example. In particular cases, there are exemplary PLGA-PEI polymers from PLGA and PEI at w/w ratios of 0.5:1, 1:1, 2:1 and 5:1, for example. In particular embodiments, the higher the PLGA content, the lower the toxicity but the lower the DNA transfection (although such may be suitable for delivery of other agents besides DNA). Particular ratios allow a suitable balance between high DNA transfection and low toxicity of the material.

In certain embodiments, there is low PLGA concentration so that PLGA-PEI (0.5:1 in w/w) is a water-soluble material, yet this lowers the cytotoxicity of PEI significantly. However, in certain cases low PLGA concentration may be suitable.

In particular cases, the PEI and primary amine concentrations of PLGA-PEI are provided and thus calculations for the structure of particular PLGA-PEI polymers are provided.

Embodiments of the invention allow easy one-step preparation of PLGA-PEI/DNA nanoparticles, self-assembly, no organic solvent or special medium, and/or no other additives besides PLGA-PEI and DNA in water or medium. Such a preparation allows for ease of large scale production.

Nanoparticles of the present invention are stable in water or medium such that there are no aggregates for many days, in at least particular embodiments. The DNA molecules (as examples of agents) are stable inside the nanoparticles. In some cases, the agent is completely encompassed in the nanoparticle, whereas in other cases the agent is not completely encompassed in the nanoparticle. The agent may be partially encompassed in the nanoparticle. In specific embodiments, nanoparticles allow slow release for cell transfection for up to 2 weeks. In aspects of the invention, PLGA-PEI/DNA is a highly efficient system with low toxicity and high transfection in vitro and in vivo.

PLGA-PEI embodiments of the invention are better than PEI with lower toxicity and better transfection. Exemplary embodiments of the invention employ PLGA-PEI to deliver GFP plasmid (as an example only) to mice, resulting in GFP expression in liver, spleen and pancreas. Compared to a standard PEI/DNA delivery system, the PLGA-PEI system is improved. Other exemplary embodiments demonstrated delivery of RFP DNA to tumors, resulting in RFP expressed in the tumor. In additional exemplary embodiments, the inventors delivered an example of a therapeutic gene to pancreas cancer that inhibited the tumor growth and even shrank the size of grown tumor.

The nanotechnology described herein has many innovative aspects including methods and compositions related to chemical reaction between PLGA and PEI; useful conditions and confirmation of PLGA modified PEI self-assembly nanoparticle formation with DNA loading; and DNA delivery efficiency and low toxicity in vitro and in vivo. The present nanotechnology is useful for applications in both scientific research and clinical practice as an efficient and safe delivery system for one or more genes or drugs or other therapeutic agents.

The nanotechnology described herein includes the synthesis of 1-(3-aminopropyl)-4-methylpiperazine (APMP) modified PLGA-PEI, APMP-PLGA-PEI. APMP is a small molecule that has been used to covalently modify other polymer materials for enhancement of biocompatibility and biodegradation properties of polymer materials. The conjugation of APMP to PLGA-PEI co-polymer enhances its transfection efficiency, in particular aspects.

Synthesis of antibody conjugated PLGA-PEI or APMP-PLGA-PEI is encompassed in the invention, including the resulting conjugate compositions. Antibodies may be directly conjugated to PLGA-PEI or APMP-PLGA-PEI, for example through bi-functional Polyethylene glycol (Maleimide-PEG-N-hydroxysuccinimide), Mal-PEG-NHS. Antibody-PLGA-PEI or antibody-APMP-PLGA-PEI can be used for the specific delivery. On the other hand, Fc binding peptide derived from Protein G or Protein A can be first conjugated to PLGA-PEI or APMP-PLGA-PEI through Mal-PEG-NHS to make a universal antibody adaptor. Fc binding peptide-PLGA-PEI or Fc binding peptide-APMP-PLGA-PEI can bind to any specific antibody for the specific delivery. One may employ HS-PEG-NHS to conjugate an antibody to this molecule, through a S—S bond.

TABLE 1

FDA Approved Antibody-based Therapeutics**

| Name: Antibody | Target: Antibody Type | Indication | Company | Approval Date |
|---|---|---|---|---|
| *OKT3: Muronomab-CD3 | CD3: Murine, IgG2a | Autoimmune | Johnson & Johnson | 1986 (US) |
| ReoPro: Abciximab | PIIb/IIIa: Chimeric, IgG1, Fab | Homeostasis | Johnson & Johnson | 1984 (US) |
| Rituxan: Rituximab | CD20: Chimeric, IgG1 | Cancer | Genentech | 1997 (US) 1998 (EU) |

TABLE 1-continued

FDA Approved Antibody-based Therapeutics**

| Name: Antibody | Target: Antibody Type | Indication | Company | Approval Date |
|---|---|---|---|---|
| *Zenapax: Daclizumab | CD25: Humanized, IgG1 | Autoimmune | Roche | 1997 (US) 1999 (EU) |
| Simulect: Basiliximab | CD25: Chimeric, IgG1 | Autoimmune | Novartis | 1998 (US) 1998 (EU) |
| Synagis: Palivizumab | RSV: Humanized, IgG1 | Infections | MedImmune | 1998 (US) 1999 (EU) |
| Remicade: Infliximab | TNFa: Chimeric, IgG1 | Autoimmune | Johnson & Johnson | 1998 (US) 1999 (EU) |
| Herceptin: Trastuzumab | HER2: Humanized, IgG1 | Cancer | Genentech/ Roche | 1998 (US) 2000 (EU) |
| *Mylotarg: Gemtuzumab ozogamicin | CD33: Humanized, IgG4, immunotoxin | Cancer | Wyeth/ Pfizer | 2000 (US) |
| Campath: Alemtuzumab | CD52: Humanized, IgG1 | Cancer | Genzyme | 2001 (US) 2001 (EU) |
| Zevalin: Ibritumomab tiuxetan | CD20: Murine, IgG1, radiolabeled (Yttrium 90) | Cancer | Biogen Idec | 2002 (US) 2004 (EU) |
| Humira: Adalimumab | TNFa: Human, IgG1 | Autoimmune | Abbott | 2002 (US) 2003 (EU) |
| Xolair: Omalizumab | IgE: Humanized, IgG1 | Autoimmune | Genentech/ Roche | 2003 (US) |
| Bexxar: Tositumomab-I-131 | CD20: Murine, IgG2a, radiolabeled (Iodine 131) | Cancer | Corixa/GSK | 2003 (US) |
| *Raptiva: Efalizumab | CD11a: Humanized, IgG1 | Autoimmune | Genentech/ Roche | 2003 (US) 2004 (EU) |
| Erbitux: Cetuximab | EGFR: Chimeric, IgG1 | Cancer | Imclone/ Lilly | 2004 (US) 2004 (EU) |
| Avastin: Bevacizumab | VEGF: Humanized, IgG1 | Cancer | Genentech/ Roche | 2004 (US) 2005 (EU) |
| Tysabri: Natalizumab | a4-Intergrin: Humanized, IgG4 | Autoimmune | Biogen Idec | 2004 (US) |
| Actemra: Tocilizumab | Anti-IL-6R: Humanized, IgG1 | Autoimmune | Chugai/ Roche | 2005 (JP) 2010 (US) |
| Vectibix: Panitumumab | EGFR: Human, IgG2 | Cancer | Amgen | 2006 (US) |
| Lucentis: Ranibizumab | VEGF: Humanized IgG1 Fab | Macular degeneration | Genentech/ Roche | 2006 (US) |
| Soliris: Eculizumab | C5: Humanized IgG2/4 | Blood disorders | Alexion | 2007 (US) |
| Cimzia: Certolizumab pegol | TNFa: Humanized, pegylated Fab | Autoimmune | UCB | 2008 (US) |
| Simponi: Golimumab | TNFa: Human IgG1 | Autoimmune | Johnson & Johnson | 2009 (US, EU, CAN) |
| Ilaris: Canakinumab | IL1b: Human IgG1 | Infalmmatory | Novartis | 2009 (US, EU) |
| Stelara: Ustekinumab | IL-12/23: Human IgG1 | Autoimmune | Johnson & Johnson | 2009 (US) 2008 (EU) |
| Arzerra: Ofatumumab | CD20: Human IgG1 | Cancer | Genmab | 2009 (EU) |
| Prolia: Denosumab | RANK ligand: Human IgG2 | Bone Loss | Amgen | 2010 (US) |
| Numax: Motavizumab | RSV: Humanized IgG1 | Anti-infective | Meddimmune | Pending |
| ABThrax: Raxibacumab | *B. anthrasis* PA: Human IgG1 | Anti-infection | GSK | 2012 (US) |
| Benlysta: Belimumab | BLyS: Human IgG1 | Autoimmune | Human Genome Sciences | 2011 (US) |
| Yervoy: Ipilimumab | CTLA-4: Human IgG1 | Cancer | BMS | 2011 (US) |
| Adcetris: Brentuximab Vedotin | CD30: Chimeric, IgG1, Drug-conjugate | Cancer | Seattle Genetics | 2011 (US) |
| Perjeta: Pertuzumab | Her2: Humanized, IgG1 | Cancer | Genentech/ Roche | 2012 (US) |
| Kadcyla: Ado-trastuzumab emtansine | Her2: Humanized, IgG1, Drug-conjugate | Cancer | Genentech/ Roche | 2013 (US) |

*Withdrawn by the sponsor
**http://www.immunologylink.com/FDA-APP-Abs.html (accessed Aug. 9, 2013; see The Immunology Link website)

TABLE 2

Chimeric monoclonal antibodies ("-xi-")**

| Type | Name contains | Examples (Clik on the name for more info) |
|---|---|---|
| Tumor | "-tuxi-" | Bavituximab, Brentuximab vedotin, Cetuximab, Siltuximab, Rituximab |
| Cardiovascular | "-cixi-" | Abciximab, Volociximab |
| Imune system | "-lixi-" | Basiliximab, Clenoliximab, Galiximab, Gomiliximab, Infliximab, Keliximab, Lumiliximab, Priliximab, Teneliximab, Vapaliximab |
| Melanoma | "-mexi-" | Ecromeximab |
| Bacterial | "-baxi-" | Pagibaximab |

Humanized monoclonal antibodies ("-zu-")

| Type | Name contains | Examples |
|---|---|---|
| Tumor | "-tuzu-" | Afutuzumab, Alemtuzumab, Bevacizumab, Bivatuzumab mertansine, Cantuzumab mertansine, Citatuzumab bogatox, Dacetuzumab, Elotuzumab, Etaracizumab, Farletuzumab, Gemtuzumab ozogamicin, Inotuzumab ozogamicin, Labetuzumab, Lintuzumab, Matuzumab, Milatuzumab, Nimotuzumab, Oportuzumab monatox, Pertuzumab, Sibrotuzumab, Tacatuzumab tetraxetan, Tigatuzumab, Trastuzumab, Tucotuzumab celmoleukin, Veltuzumab |
| Immune system | "-lizu-" | Immunosuppressive: Aselizumab, Apolizumab, Benralizumab, Cedelizumab, Certolizumab pegol, Daclizumab, Eculizumab, Efalizumab, Epratuzumab, Erlizumab, Fontolizumab, Mepolizumab, Natalizumab, Ocrelizumab, Omalizumab, Pascolizumab, Pexelizumab, PRO 140, Reslizumab, Rontalizumab, Rovelizumab, Rupilizumab, Siplizumab, Talizumab, Teplizumab, Tocilizumab, Toralizumab, Vedolizumab, Visilizumab, TGN1412<br>Non-immunosuppressive: Ibalizumab |
| Bacterial | "-bazu-" | Tefibazumab |
| Cardiovascular | "-cizu-" | Alacizumab pegol, Bevacizumab/Ranibizumab, Etaracizumab, Tadocizumab |
| Nervous system | "-nezu-"/ "-neuzu-" | Bapineuzumab, Solanezumab, Tanezumab |
| Toxin target | "-toxazu-" | Urtoxazumab |
| Viral | "-vizu-" | Felvizumab, Motavizumab, Palivizumab |
| Inerleukin | "-kizu-" | Lebrikizumab |
| Angiogensis | "-anibizu-" | Ranibizumab |

Fully Human monoclonal antibodies ("-u-")

| Type | Name contains | Examples |
|---|---|---|
| Tumor | "-tumu-"/ "-tu-" | Adecatumumab, Belimumab, Cixutumumab, Conatumumab, Figitumumab, Iratumumab, Lexatumumab, Lucatumumab, Mapatumumab, Necitumumab, Ofatumumab, Olaratumab, Panitumumab, Pritumumab, Robatumumab, Votumumab, Zalutumumab |
| Immune system | "-limu-" | Immunosuppression: Adalimumab, Atorolimumab, Fresolimumab, Golimumab, Lerdelimumab, Metelimumab, Morolimumab immune<br>Activation: Ipilimumab, Tremelimumab<br>Other: Bertilimumab, Zanolimumab |
| Bacterial | "-bacu-" | Nebacumab, Panobacumab, Raxibacumab |
| Bone | "-osu-" | Denosumab |
| Nervous system | "-neru-" | Gantenerumab |
| Musculo-skeletal | "-mulu-" | Stamulumab |
| Viral | "-viru-" | Exbivirumab, Foravirumab, Libivirumab, Rafivirumab, Regavirumab, Sevirumab, Tuvirumab |
| Inerleukin | "-kinu-" | Briakinumab, Canakinumab, Ustekinumab |
| Fungal | "-fungu-" | Efungumab |
| Cardiovascular | "-ciru-" | Ramucirumab |

**http://www.immunologylink.com/FDA-APP-Abs.html (accessed Aug. 9, 2013; see The Immunology Link website)

II. Therapeutic or Other Agents

In embodiments of the invention, the nanotechnology delivery system allows delivery of one or more therapeutic or other agents (including, for example, diagnostic agents) to an individual in need of the agent(s). The system, in particular cases, allows delivery of more than one agent, and such multiple agents may be of the same type of agent (nucleic acid or drug, for example) or not. Thus, in a plurality of nanoparticles, there may be a mixture of nanoparticles with more than one agent but with each separate nanoparticle having only one agent; a therapeutically effective amount of the agent may be provided to the individual. In some embodiments, there are may be a mixture of nanoparticles with more than one agent but with a particular nanoparticle having more than one agent. In any case, a therapeutically effective amount of the agent may be provided to the individual.

The agent may be of any kind so long as the PLGA-PEI nanoparticles may stably comprise the agent. The agent(s) may interact with DNA, in specific embodiments. In specific cases, the agent is one or more of a nucleic acid, small molecule, protein, peptide, or mixture thereof. The agent may be a drug. Particular nucleic acid examples include oligonucleotides, miRNA, shRNA, siRNA, DNA, RNA, mRNA, cDNA, double stranded nucleic acid, single stranded nucleic acid, and so forth. The size of the nucleic acid may be as large as a large plasmid or as small as a small oligonucleotide, as examples only. In some cases, the DNA is a vector comprising an expression construct for expression of one or more therapeutic polynucleotides or one or more polynucleotides that encodes a therapeutic gene product.

In some embodiments, the therapeutic gene product is an entity that reduces at least in part if not in full the expression of an oncogene. Examples of oncogenes include Trop2, ZIP4, mesothelin, cyclophilin A, miR-196a, miR-363, and the agent may reduce expression of one or more of these genes in part or in full. Examples of the agent could be anti-sense RNA, miRNA oligo, or shRNA to silence a gene. In other cases, the agent targets a tumor suppressor gene, and the agent increases expression of the tumor suppressor gene. Examples of tumor suppressors include XIST, Jade-2 or miR-198.

Particular small molecules may include those utilized as drugs for a medical condition. Regarding small molecule drug delivery, the PLGA-PEI/DNA nanoparticles can be used for delivery vehicles for small molecules such as drugs for chemotherapy and other purposes. Hydrophilic drugs and/or hydrophobic small molecule drugs may be utilized, and the small molecule drugs may directly interact with the DNA and/or PEI portion of the nanoparticles for drug delivery. Drugs containing amino groups in their structure are usually positively charged that can interact with negatively charged DNA molecules. Drugs containing —COOH, —$PO_4^-$ or other acidic groups in their structure can interact with the amino groups in PEI portion of the nanoparticles. Nucleoside analog drugs can also be loaded with PLGA-PEI/DNA nanoparticles. Based on chemical structures, PLGA-PEI/DNA nanoparticles are an efficient delivery system for many drugs including at least gemcitabine, AraC, PALA, vincristine, methitreate, vinblastine, paclitaxel, vinorelbine, topotecan, cisplatin, doxorubicin, daunomycin, etc.

Most importantly, one can use PLGA-PEI, APMP-PLGA-PEI or antibody-PEG-PLGA-PEI (as examples) to deliver genes and chemotherapeutic drugs for gene therapy and chemotherapy combination. PLGA-PEI can easily form nanoparticles with DNA, and many small molecule drugs can interact with either DNA or PEI portion of the PLGA-PEI/DNA nanoparticles to form complexes. Therefore, DNA and drugs could be delivered in the same time to the same place for a combination therapy. Simply, one can mix PLGA-PEI, small molecule drug and the gene to be delivered together in a desired ratio to prepare nanoparticles.

In certain embodiments, the agent is a protein or peptide. The protein or peptide may be therapeutic and/or diagnostic.

Figure 1B:
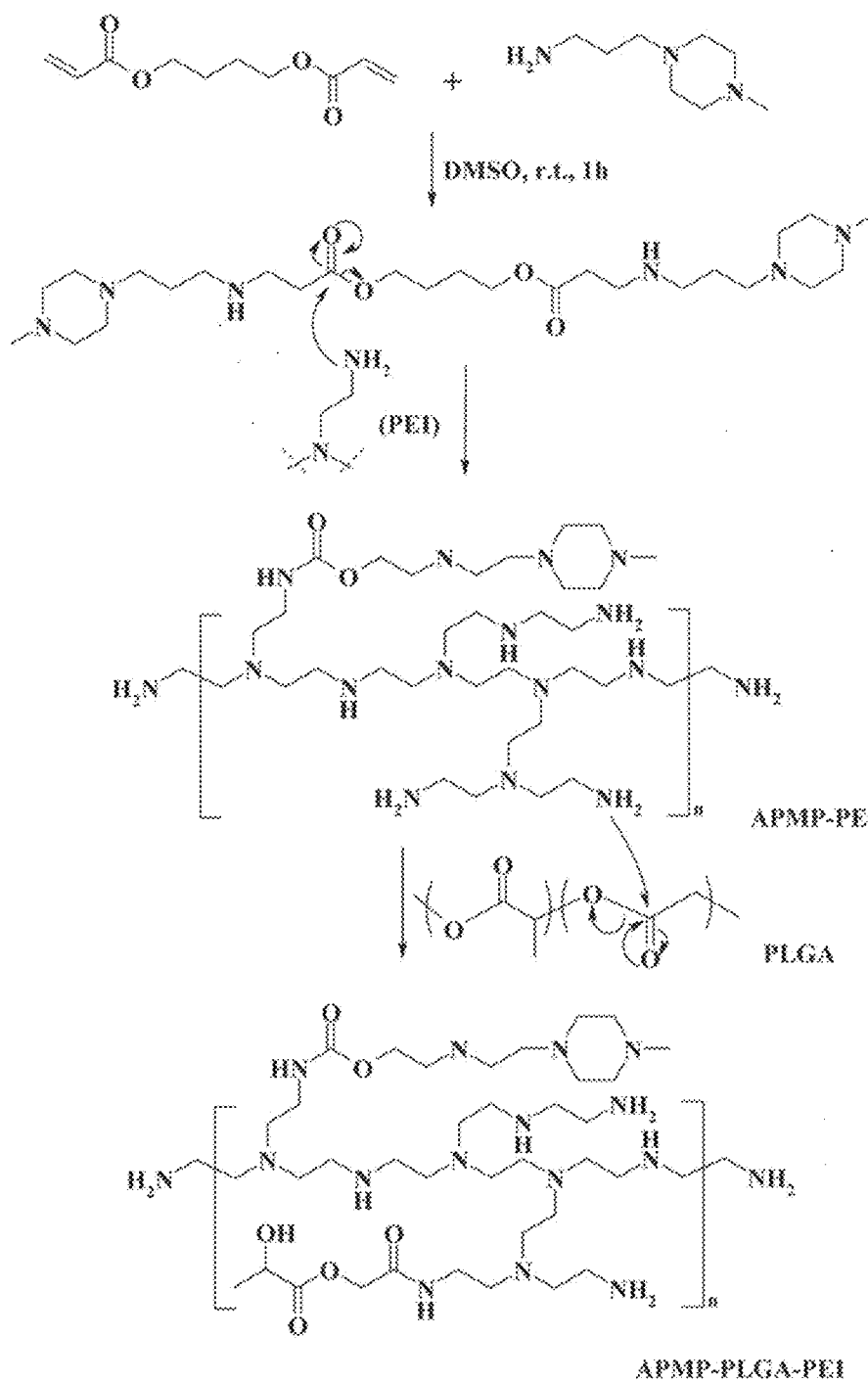
Figure 1C:
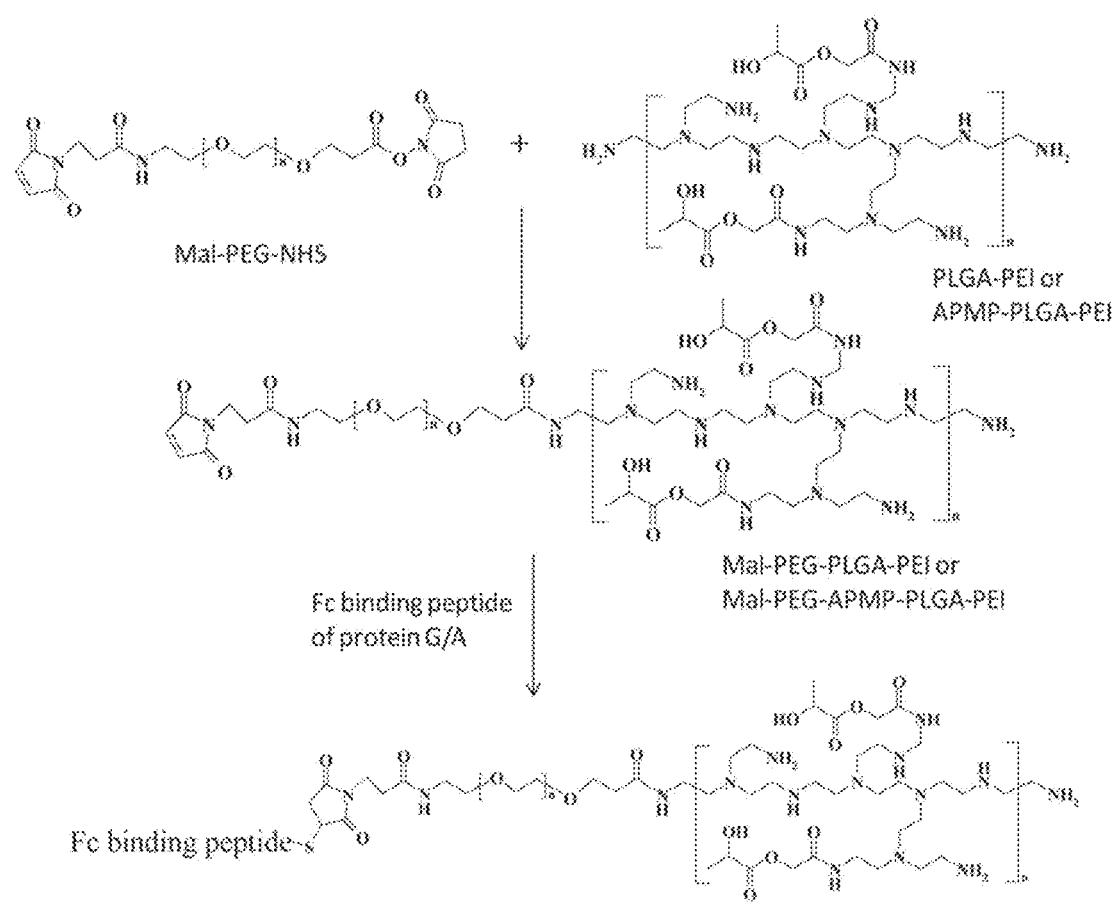

In certain cases the protein is a protein naturally endogenous to the individual to which the protein is delivered, but the endogenous level is deficient or naturally insufficient or would be beneficial to be present or abundant above a natural level. Proteins or peptides may be delivered by adaptor peptide-PEG-PLGA-PEI (FIG. 1C). The sequence of an adaptor peptide may be CGGGGDCAWHLGELVW-CTGGGGC (SEQ ID NO:1), both sides are ended with cystine. One side is conjugated to PEG-PLGA-PEI, while the other side is used to conjugate with cystine in delivering protein or peptide through a S—S bond formed from the oxidation of sulfhydryl (—SH) groups of cystines. Oxidants such as hydrogen peroxide, iodine in the presence of base or several metals including copper(II) and iron(III) complexes can be used in the preparation. Once the protein or peptide is conjugated to PLGA-PEI via disulfide bond, the nanoparticle can be prepared with functional or non-functional DNA. When the nanoparticles are delivered into the cell by endocytosis, lysosome enzyme can cut the disulfide bond and thus release the protein or peptide to the cytosol or nucleus for the function (Collins et al, 1991; Arunachalam et all, 2000).

In other embodiments, any amino acid can be conjugated to a molecule—PLGA-PEI through an amide linkage, although the reaction would need activation. For example, if a C-terminal of the peptide is esterized, then the peptide can directly conjugate to PEI (with free —NH2) through an amide linkage, in specific cases.

The agent(s) employed in the nanoparticle may be useful for any kind of medical condition. In specific embodiments, the medical condition is cancer, such as brain, lung, breast, prostate, pancreatic, kidney, colorectal, blood, bone, stomach, spleen, gall bladder, testicular, ovarian, cervical, pituitary gland, thyroid gland, skin, and so forth. In some embodiments, the medical condition is for treatment of an infection from a pathogen, including bacteria, virus, fungus, and so forth. The medical condition may be an injury or wound. Other therapeutic agents include painkillers, diuretic, diabetic drugs, acid reflux drugs, high blood pressure drugs, thyroid hormone, high cholesterol drugs, and so forth. The medical condition may be heart disease, kidney disease, stroke, respiratory disease, septicemia, and so forth.

Other agents may be employed that are not therapeutic. In certain cases, one may employ the nanotechnology to deliver one or more diagnostic agents. Such an agent may have a label, for example, that allows it to be tracked within an individual's body. In specific embodiments, there are fluorescent microspheres and nanoparticles for imaging. Exemplary labels and colors include blue, green, orange, red and near-IR.

In some embodiments, the agent is to be employed systemically throughout the body, although in specific cases the agent is to be employed locally in a body.

Besides human diseases, the nanoparticle delivery system can be also used in the treatment of animal diseases and in research in microorganisms, cell cultures and animal models, for example.

III. Delivery of the PLGA-PEI Complex

Embodiments of the nanotechnology PLGA-PEI complex of the disclosure may be delivered to an individual in need thereof in a variety of suitable ways. In specific embodiments, the complex can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the foregoing as would be known to one of ordinary skill in the art.

Vaccines including microorganisms and specific antigens can be delivered by the PLGA-PEI nanotechnology, in at least particular cases. Examples of vaccines include those for cancer or infection, such as infection by a microbe. Examples of vaccines include live, attenuated vaccines; inactivated vaccines; subunit vaccines; toxoid vaccines; conjugate vaccines; DNA vaccines; and recombinant vector vaccines. Examples of vaccines include vaccines against hepatitis of any kind, rotavirus, DTaP, HIB, polio, MMR, and so forth.

The actual dosage amount of a composition of the present invention administered to an animal or patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

IV. Combination Treatments

In certain embodiments of the invention one or more medical treatments may be provided to an individual in addition to the PLGA-PEI nanoparticle that itself comprises a therapeutic agent. The one or more other medical treatments may be suitable for cancer therapy, bacterial or viral infection, inherited diseases, or any other kind of medical condition.

In specific embodiments, the combination therapy comprises one or more anti-cancer agents. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cells with the nanoparticle and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the nanoparticles and the other includes the second agent(s).

In the context of the present invention, it is contemplated that the nanoparticle therapy could be used similarly in conjunction with chemotherapeutic, radiotherapeutic, or immunotherapeutic intervention, for example. Alternatively, the nanoparticle therapy may precede or follow the other agent treatment by intervals ranging from minutes to weeks. In embodiments where the other agent and nanoparticles are applied separately to the cell, one would generally ensure that a significant period of time did not expire between the time of each delivery, such that the agent and expression construct would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Various combinations may be employed, such as wherein nanoparticle therapy is "A" and the secondary agent, such as radio- or chemotherapy, is "B":

A/B/A B/A/B B/B/A A/A/B A/B/B B/A/A A/B/B/B B/A/ B/B

B/B/B/A B/B/A/B A/A/B/B A/B/A/B A/B/B/A B/B/A/A B/A/B/A B/A/A/B A/A/A/B B/A/A/A A/B/A/A A/A/B/A

Administration of the therapeutic nanoparticles of the present invention to a patient will follow general protocols for the administration of chemotherapeutics, in some cases. It is expected that the treatment cycles would be repeated as necessary. It also is contemplated that various standard therapies, as well as surgical intervention, may be applied in combination with the described hyperproliferative nanoparticle therapy. The present invention has similar clinical applications to animal diseases.

A. Chemotherapy

Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin and methotrexate, or any analog or derivative variant of the foregoing.

B. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

C. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with Ad-mda7 gene therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

D. Gene Therapy

In yet another embodiment, the secondary treatment is a secondary gene therapy in which a second therapeutic polynucleotide is administered before, after, or at the same time a first therapeutic polynucleotide encoding all of part of a therapeutic polypeptide or wherein the polynucleotide is therapeutic itself (such as miRNA, siRNA, shRNA). Delivery of a vector encoding either a full length or truncated therapeutic polypeptide or a therapeutic polynucleotide in conjunction with nanoparticles of the present disclosure will have a combined anti-hyperproliferative effect on target tissues.

E. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

F. Other Agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyerproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

V. Kits of the Invention

Any of the compositions described herein may be comprised in a kit. In a non-limiting example, PLGA, PEI, APMP, Fc binding peptide, and/or one or more therapeutic or other agents may be comprised in a kit. Any linker to conjugate the nanoparticle to another compound may be included. The kit will comprise its components in suitable container means. Such components may be suitably aliquoted. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a container. The kits of the present invention also will typically include a means for containing the component containers in close confinement for commercial sale. Such containers may include injection or blow-molded plastic containers into which the desired vials are retained.

When the components of the kit are provided in one and/or more liquid solutions, the liquid solution may be an aqueous solution, with a sterile aqueous solution being particularly preferred. The compositions may also be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit.

However, the components of the kit may be provided as dried powder(s). When reagents and/or components are provided as a dry powder, the powder can be reconstituted by the addition of a suitable solvent. It is envisioned that the solvent may also be provided in another container means.

Irrespective of the number and/or type of containers, the kits of the invention may also comprise, and/or be packaged with, an instrument for assisting with the injection/administration and/or placement of the ultimate composition within the body of an animal. Such an instrument may be a syringe, pipette, forceps, and/or any such medically approved delivery vehicle.

VI. Pharmaceutical Preparations

Pharmaceutical compositions of the present invention comprise an effective amount of one or more compositions that in some embodiments are dissolved or dispersed in a pharmaceutically acceptable carrier. Embodiments of the disclosure encompass drug (or any therapeutic and/or diagnostic agent) encapsulation into microspheres and nanoparticles, microemulsions (for example, to deliver insoluble active pharmaceutical ingredients (API) or oily API), nanoparticles (surface modifications, coatings and conjugation, for example), and administration (oral, sublingual, injectable, subcutaneous, inhalation, and/or topical, for example) of same. In specific embodiments, pharmaceutical preparations include controlled release and sustained release of a drug (or any therapeutic and/or diagnostic agent).

The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one composition or additional active ingredient will be known to those of skill in the art in light of the present disclosure, as exemplified by Remington: The Science and Practice of Pharmacy, 21$^{st}$ Ed. Lippincott Williams and Wilkins, 2005, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The composition may comprise different types of carriers depending on whether it is to be administered in solid, liquid or aerosol form, and whether it need to be sterile for such routes of administration as injection. The present invention can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The composition may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present invention, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that includes the composition, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the composition may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

A. Alimentary Compositions and Formulations

In preferred embodiments of the present invention, the compositions are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792, 451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

B. Parenteral Compositions and Formulations

In further embodiments, the composition may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 6,613,308, 5,466,468, 5,543,158; 5,641,515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in isotonic NaCl solution and either added hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

C. Miscellaneous Pharmaceutical Compositions and Formulations

In other preferred embodiments of the invention, the active compound may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Preparation of PLGA-PEI Copolymer

Poly(lactic-co-glycolic acid) (PLGA) is a Food and Drug Administration (FDA) approved material, which is used for therapeutic devices and delivery systems because of its biodegradability, biocompatibility, low toxicity and excellent pharmacokinetic parameters. For example, PLGA as a drug delivery nanoparticle can avoid elimination by the reticuloendothelial system and stay a long time in the circulation. However, PLGA is not efficient to load nucleic acid because of its chemical properties. Polyethylenimine (PEI) can effectively bind and condense nucleic acid, and form nanoparticles via electrostatic interactions between negatively charged nucleic acid phosphate groups and positively charged PEI amine groups. PEI can deliver DNA into cells through endocytosis and release DNA in pH-dependent fashion (Utsuno and Uludg, 2010; Sun et al., 2011; Sun et al., 2012). Branched PEI (25 KDa) is one of the most commonly used transfection regents. However, PEI lacks biodegradable moieties and can cause high cell toxicity (Akinc et al., 2005; Moghimi et al., 2005). Transfection rate of PEI is also variable in different types of cells. Pharmacokinetic parameters of PEI as a nucleic acid delivery system in vivo are not favorable.

Thus, combining PLGA to PEI could produce new co-polymers which have better properties for nucleic acid delivery including high DNA load capacity, effective DNA delivery and release to broad cell types, improved pharmacokinetics and low toxicity. Degradable versions of PEI have shown improved transfection efficacy and lower cytotoxicity than nondegradable versions (Green et al., 2007; Forrest et al., 2003). For this purpose, there is described herein a new methodology to produce a new PLGA-PEI co-polymer that has unique chemical structure and properties for delivering agents, such as nucleic acid.

PLGA-PEI co-polymer was prepared directly by mixing PLGA and PEI in organic solvent under the following exemplary conditions. PLGA (12-16 kDa, lactide:glycolide 50:50 mol/mol, inherent viscosity 0.50-0.65) was obtained from Polysciences, Inc. (Warrington, Pa.). PEI, branched with average MW ~25 kDa, and tetrahydrofuran (THF) were obtained from Sigma-Aldrich (St. Louis, Mo.). Typically, 250 mg PEI and 120 mg PLGA dissolved in 10 ml THF, respectively, are mixed under moderate stirring at room temperature (23° C.) for 48 hours. The soft precipitate is separated from the THF solution and washed with THF solvent two times. The solid is then dried in vacuum at room temperature overnight. This makes a co-polymer PLGA-PEI (w/w 0.5/1). Four types of PLGA-PEI copolymer are prepared at PLGA/PEI weight ratios of 0.5:1, 1:1, 2.5:1, and 5:1, corresponding molar ratios of 1:1, 2:1, 5:1 and 10:1, respectively. The higher the ratio, the better the solubility of co-polymer is in THF, while the poorer the solubility is in water. The procedure of using PLGA and PEI at the weight ratio 0.5:1 yields the co-polymer conjugate containing on average 1 PLGA molecule per PEI molecule approximately. For co-polymer PLGA-PEI (w/w 0.5/1), the PEI concentration in PLGA-PEI co-polymer conjugate is determined as 64.7±1.6% by using a copper sulfate assay (von Harpe et al., 2000) and the primary amine concentration is measured as 49±3% by the TNBS assay (Bullock et al., 1997). For PLGA-PEI (w/w 1:1), the PEI concentration in PLGA-PEI co-polymer conjugate was determined as 48.0±0.8%, and the primary amine concentration is measured as 9.5±2.1%. For PLGA-PEI (w/w 2:1) and PLGA-PEI (w/w 5:1), the primary amine concentration is determined as 11.3% and 8.2%, respectively (Table 3).

TABLE 3

PEI concentration and primary amine percentage in different formations of PLGA-PEI. The procedures for PLGA to PEI at weight ratio 0.5:1 yielded conjugates containing on average 1 PLGA per PEI molecule approximately. The PEI concentration in PLGA-PEI conjugates was determined as 64.7 ± 1.6% using a copper sulfate assay and the primary amine concentration was measured as 49 ± 3% by the TNBS assay.

| Polymers | PEI concentration | PLGA concentration | —NH2% |
| --- | --- | --- | --- |
| PLGA-PEI (0.5:1) | 64.7 ± 1.6% | 35.3% | 49 ± 3% |
| PLGA-PEI (1:1) | 48.0 ± 0.8% | 52% | 9.5 ± 2.1% |
| PLGA-PEI (2:1) | 32.3 ± 1.4% | 68% | 11.3 ± 0.1% |
| PLGA-PEI (5:1) | 15.7 ± 0.6% | 84% | 8.2 ± 0.2% |
| APMP-PLGA-PEI | 60.9 ± 1.4% | 39% | 51.5 ± 0.8% |

Based on the analyses of weight ratio and primary amine of the new co-polymer of PLGA-PEI, one can confirm its chemical structure. Each branched PEI molecule (25 kDa) has about 214 primary amines, 159 secondary amines and 212 tertiary amines. While each PLGA molecule (12~16 kDa) has average of 215 (184 to 246) ester bonds. Based on the molecular weights of PLGA and PEI and PEI concentration (64.7±1.6%) in PLGA-PEI (0.5:1 w/w), the PLGA-PEI (0.5:1 w/w) polymers contain 1 starting PLGA per PEI molecule approximately. Its primary amine concentration is measured as 49±3%, indicating half of the primary amines reacted with PLGA by attacking its ester bonds and resulted in formation of amide (FIG. 1A). Starting PLGA molecule is fragmented into lactide-co-glycolide single units by PEI, while PEI is intact; thus about 109 lactide-co-glycolide single units are conjugated to one PEI molecule by amide linkage. This chemical structure of PLGA-PEI co-polymer is a new material that has not been determined previously.

Example 2

Preparation of APMP Modified PLGA-PEI Copolymer 1-(3-aminopropyl)-4-methylpiperazine (APMP, Alfa Aesar, Ward Hill, Mass.) is a small molecule, which has been used to covalently modify other polymer materials for enhancement of biocompatibility and biodegradation properties of polymer materials (Bhise et al., 2010; Sunshine et al., 2012; Sunshine et al., 2012; Eltoukhy et al., 2012; Sunshine et al., 2009; Lee et al., 2009). However, it has not been used to modify PLGA or PEI for enhancing delivery efficacy. In aspects of the disclosure, the conjugation of APMP to PLGA-PEI co-polymer enhances its transfection efficiency.

APMP can be directly conjugated to PEI through a linker and enhance the transfection of PEI by modifying its bioavailability, biodegradation and lowering its toxicity. In order to conjugate APMP to PEI, APMP first reacts to 1,4-butanediol diacrylate in DMSO for 2 h to make a 1,4-butanediol diacrylate-co-1-(3-aminopropyl)-4-methylpiperazine, (Sunshine et al., 2012), which has ester bonds for reacting with primary amines of PEI in THF for 24 h. Thus, APMP is conjugated to PEI through a short linker forming a new co-polymer material APMP-$CH_2CH_2$—CO-PEI. The content of APMP is based on the desired molar ratio in the final conjugate. In this material, APMP-$CH_2CH_2$—CO— occupies small amount of primary amines of PEI, thus, APMP-$CH_2CH_2$—CO-PEI can further react with PLGA in a desired ratio in THF for 48 h to make an APMP-PLGA-PEI (FIG. 1B). The soft precipitate is separated from the THF solution and washed with THF solvent for two times. The solid is then dried in vacuum at room temperature overnight. The PEI concentration is determined based on the Cu(II) method analysis (von Harpe et al., 2000), and the primary amine in this modified PLGA-PEI is measured by the TNBS assay (Bullock et al., 1997). Functionally, APMP-PLGA-PEI can effectively load DNA and form nanoparticles in aqueous solution. More importantly, APMP-PLGA-PEI is more effective to deliver DNA into cells. Based on this principle, several other compounds can be used to modify PLGA-PEI including 2-(3-aminopropylamino)ethanol, 2-methyl-1,5-diaminopentane, 1-(3-aminopropyl)pyrrolidine, 4-aminophenyl disulfide and cystamine (Bhise et al., 2010; Sunshine et al., 2012).

Alternatively, APMP modified PLGA-PEI co-polymer (APMP-PLGA-PEI) is also prepared in the order of mixing APMP and PLGA first for one day, then mixing with PEI for additional 2 days in THF solution. APMP has a primary amine, which can aminolyze PLGA, thus conjugating to PLGA. When this APMP modified PLGA (polyester) mixes with PEI, the primary amines in PEI will attack ester bonds of PLGA, therefore, forming an APMP modified PLGA-PEI. Typically, 20 mg APMP and 120 mg PLGA dissolved in 5 ml THF, respectively, are mixed under a moderate stirring rate and stirred at room temperature for 20 hours. This mixture is added into 250 mg branched PEI in 5 ml THF and stirred at room temperature for 48 hours. The soft precipitate is separated from the THF solution and washed with THF solvent for two times. The solid is then dried in vacuum at room temperature overnight. The PEI concentration is about 60% based on the Cu(II) method analysis (von Harpe et al., 2000), and the primary amine in this modified PLGA-PEI is 51.5±0.8% (Bullock et al., 1997). So, based on this data, about 4% APMP is incorporated in PLGE-PEI.

Example 3

Preparation of Antibody-Binding PLGA-PEI Copolymer

Antibodies are profoundly used targeting moieties for specific drug deliveries due to their high selectivity, affinity and variability to their targets (Arruebo et al, 2009; Bae et al, 2012; Kang et al, 2012). Antibodies are usually directly conjugated to the surface of the delivery platforms. However, chemical conjugations often impair the binding capability of antibodies due to alterations in their antigen binding sites, denaturation, or random orientation of the antibodies. Therefore, more effective methods are developed to couple antibodies and delivery platforms without changing the properties of the antibodies. Protein A/G is widely used for antibody purifications by non-covalently capture antibodies by specifically binding to the fragment crystallizable region (Fc) of antibodies, thus structure and function of the antibodies retain fully intact (Bae et al, 2012; Kang et al, 2012). Small binding peptides mimicking Fc binding peptide of protein G or protein A can be used in the design of the delivery system, which can provide an adaptor to bind any antibody for specific delivery.

The exemplary small binding peptide, DCAWHLGELVWCT (SEQ ID NO:2) derived from protein G, has a high affinity to antibodies and has been inserted into a protein cage to bind antibodies (Kang et al, 2012). Extra glycine residues were added to both sides of the binding peptide to enhance their conformational flexibility and to provide full access to approaching antibodies. One can synthesize this Fc binding peptide in 1 or more than 1 copy to enhance the binding force. Extra glycine residues may be added and ended up with cystine in both sides of the binding peptide, e.g., 1 copy: CGGGGDCAWHLGELVW-CTGGGGC (SEQ ID NO:1); 2 copies: CGGGGD-CAWHLGELVWCTDCAWHL-GELVWCT GGGGC (SEQ ID NO:3). The cystine in one end may be used to conjugate the peptide to PLGA-PEI through bi-functional PEG, Mal-PEG-NHS (FIG. 1C).

One can use bi-functional PEG (Mal-PEG-NHS) to connect antibody or Fc binding peptide fragment to PLGA-PEI to make a specific delivery reagent. Mal-PEG-NHS reacts with PLGA-PEI at a desired molar ratio in 0.1 M phosphate buffer (pH 7.0) at room temperature for 3 h under nitrogen, in specific embodiments. The Mal-PEG-PEI-PLGA may be purified by gel-permeation chromatography, for example. The antibody or Fc binding peptide fragment may be added to the Mal-PEG-PEI-PLGA at a desired molar ratio and react at room temperature overnight under argon. The antibody-PEG-PEI-PLGA may be further purified by dialysis against 0.1 M NaCl.

Example 4

Preparation of PLGA-PEI/DNA Nanoparticles

Both PLGA-PEI (w/w up to 1:1) and APMP modified PLGA-PEI (w/w=0.5:1) dissolve in water very well. These highly positive charged polymers are suitable for gene delivery. PLGA-PEI/DNA nanoparticles are prepared in different ratios of polymer to DNA (usually from 1.5:1 to 25:1) by adding plasmid DNA solution to water solution of PLGA-PEI polymer, followed by vortexing for 5 s. Typically, 10 μg plasmid DNA in 50 μl of water is added to 25 μg of PLGA-PEI in 50 μl water and vortexed for 5 s. These nanoparticle dispersions are kept at room temperature for 30 min before use. These nanoparticle dispersions are used without further treatment. APMP-PLGA-PEI/DNA nanoparticles are prepared likewise. Similarly, for gene therapy and chemotherapy combination, the DNA to be delivered is mixed with PLGA-PEI, APMP-PLGA-PEI or antibody-PEG-PLGA-PEI together chemotherapeutic drugs to prepare nanoparticles. PLGA-PEI or APMP-PLGA-PEI can load a wide range of DNA, for example, 25 ug PLGA-PEI can deliver 1 to 15 ug DNA to cells in 1 well of a 6-well plate and transfect high efficiently with less toxicity than lipofectamine 2000 and PEI.

For nanoparticles formed with PLGA-PEI (0.5:1 w/w) and DNA, the effective diameters of the nanoparticles range from 100 nm to 130 nm depending on the ratios of PLGA-PEI to DNA (Table 4).

TABLE 4

Characterization of PLGA-PEI/DNA nanoparticles. The sizes of PLGA-PEI/DNA nanoparticles were determined by dynamic light scattering using ZetaPlus Particle Sizing, Brookhaven Instruments Corp.

| | Effective diameter (nm) | Polydispersity | Mean diameter (nm) | Zeta potential (mV) |
|---|---|---|---|---|
| 5 ug PLGA-PEI/10 ug DNA | 119.4 ± 1 | 0.313 | 180.7 | −38.9 ± 3.3 |
| 10 ug PLGA-PEI/10 ug DNA | microparticle | N/A | N/A | N/A |
| 15 ug PLGA-PEI/10 ug DNA | 104 ± 0.8 | 0.12 ± 0.04 | 116± | 30 ± 1.4 |
| 20 ug PLGA-PEI/10 ug DNA | 128 ± 26 | 0.27 ± 0.08 | 177 ± 20 | 22 ± 8 |
| 25 ug PLGA-PEI/10 ug DNA | 108 ± 1.2 | 0.27 ± 0.08 | 115± | 21.4 ± 0.4 |
| 35 ug PLGA-PEI/10 ug DNA | 100.3 ± 1.3 | 0.157 | 110 | 27.5 ± 4.3 |
| 10 ug PEI/10 ug DNA | 164.2 ± 1.9 | 0.23 | 202.6 | 57.5 ± 1.5 |
| 20 ug PEI/10 ug DNA | 156.5 ± 1.6 | 0.189 | 204.8 | 63.8 ± 4.6 |

Figure 2:
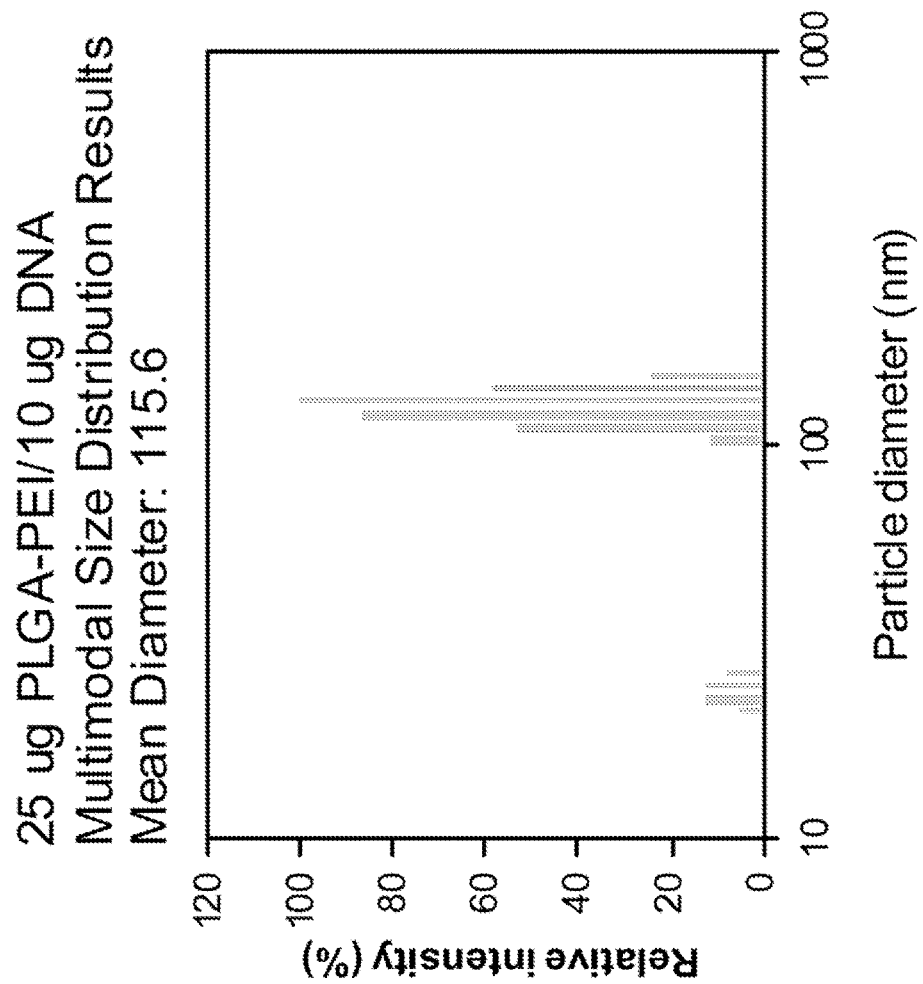
FIG. 2 shows multimodal size distribution results with 25 μg PLGA-PEI/10 μg plasmid DNA (double stranded).

A representative size distribution for 25 μg PLGA-PEI/10 μg DNA is shown in FIG. 2. Polydispersity is between 0.1 and 0.3. The zeta potential of PEI only is up to 90 mV, but decreases to 60 mV if complexed with DNA. Compared to PEI/DNA, the PLGA-PEI/DNA has a much less zeta potential that is around 20 mV, indicating the positive charge of PEI is effectively shielded by PLGA. Particle size distribution and zeta potential of APMP modified PLGA-PEI/DNA are listed in Table 5.

TABLE 5

Size and zeta potential of APMP-PLGA-PEI/DNA nanoparticles. The sizes of PLGA-PEI/DNA nanoparticles were determined by dynamic light scattering using ZetaPlus Particle Sizing, Brookhaven Instruments Corp.

| | Effective diameter (nm) | Polydispersity | Mean diameter (nm) | Zeta potential (mV) |
|---|---|---|---|---|
| 5 ug APMP-PLGA-PEI/10 ug DNA | aggregates | | | 19.6 ± 1.3 |
| 10 ug APMP-PLGA-PEI/10 ug DNA | 431.6 ± 9.8 | 0.291 | 658.4 | 32.2 ± 1.7 |
| 15 ug APMP-PLGA-PEI/10 ug DNA | 118.1 ± 0.2 | 0.2 | 147 | 35.4 ± 1.0 |
| 20 ug APMP-PLGA-PEI/10 ug DNA | 136.4 ± 0.8 | 0.2 | 161 | 43.3 ± 0.3 |
| 25 ug APMP-PLGA-PEI/10 ug DNA | 139.2 ± 0.6 | 0.24 | 194 | 45 ± 0.7 |
| 30 ug APMP-PLGA-PEI/10 ug DNA | 140.7 ± 0.6 | 0.2 | 168 | 47.8 ± 2.2 |
| 35 ug APMP-PLGA-PEI/10 ug DNA | 137.2 ± 2.1 | 0.22 | 171 | 50 ± 2.4 |

For the reaction time of PLGA with PEI or APMP-PEI in a weight ratio of 0.5:1, the inventors have observed that reaction starts immediately at room temperature after mixing in THF because the solution becomes unclear, i.e., products do not dissolve in THF. All products precipitate in 48 h. One can test the properties of the product if one stops the reaction at short time such as 1 h, 5 h or 24 h yet. The reaction time is important, in specific embodiments of the invention. Because PEI breaks large PLGA to small lactide-co-glycolide single units conjugated to PEI, the final product has different solubility in THF from the reactants (PLGA and PEI). If the reaction is stopped in 1 h, 5 h, or 24 h, the reaction has not finished, in certain embodiments, and thus the product may have different structures from those provided herein. In most of the literature, PLGA and PEI are mixed in organic solvent for less than 1 h before pouring into surfactant solutions (Bivas-Benita et al., 2004; Nam et al., 2003; Shau et al., 2012; Gargouri et al., 2011; Bivas-Benita et al., 2009). In the literature, no paper reported the final structure of PLGA and PEI mixture. In embodiments of the invention, different reaction times may make different products. In the present technology, the PLGA and PEI react in 48 h and the reaction is complete, therefore, the uniform product is formed.

For reaction temperature, one can test the reaction at lower or higher temperature. For the starting material PLGA, PLGA (50:50) (12-16 kDa, lactide:glycolide 50:50 mol/mol, i.v. 0.50-0.65) and PLGA (50:50, 110 kDa) was used. A uniform product is produced. In specific embodiments, other PLGA with different molecular weights and lactide:glycolide ratios make similar materials but some properties may be slightly different. One can synthesize PLGA-PEI with different PLGA polymers. For PEI, in particular embodiments it is branched with multiple primary amines. However, branched PEI also has different molecular weights including (not limited to) 800, 1200, 1800, 2500, 5000, 25000 and 60000 kDa, from commercial sources.

The PLGA to PEI ratio is another factor that impacts the product properties. Branched PEI is a good DNA delivery vector, but it is too toxic. PLGA was used to modify PEI by conjugating PLGA single units to PEI to lower its toxicity and improve delivery property/or process. If the PLGA to PEI ratio is too high, the primary amine of PEI will be mostly occupied by PLGA fragments, thus DNA load capacity and transfection efficiency will be decreased. If it is too low, however, the PEI is not well shielded by PLGA fragments, the co-polymer may still have high toxicity to cells. A particular condition of PLGA to PEI ratio may be useful. Furthermore, the literature methods used less than 15% PEI to prepare PLGA-PEI (Bivas-Benita et al., 2004; Nam et al., 2003; Shau et al., 2012; Gargouri et al., 2011; Bivas-Benita et al., 2009). The structures of PLGA-PEI prepared with less PEI content are completely different from those prepared with high PEI content. For example, in the present material PLGA-PEI (0.5/1 w/w), about 50% primary amines of PEI are conjugated with PLGA lactide-co-glyctide single units via amide linkage; the other 50% primary amines of PEI are still free. If the PLGA to PEI ratio is increased to 1:1 or above (w/w), 90% of primary amines of PEI are occupied by PLGA fragments. Besides, the PLGA fragments can become bigger if more PLGA content or less PEI content is used, resulting in different structures.

An APMP modified PLGA-PEI was synthesized that has better delivery properties than PLGA-PEI and that lacks APMP. APMP has been conjugated to other polymers to increase the cell uptake (Sunshine et al., 2012). Other chemicals with similar properties to APMP can also be conjugated to PLGA-PEI to deliver nucleic acids and other molecules to cells or animals. One can synthesize modified PLGA-PEI with 2-(3-aminopropylamino)ethanol, 2-methyl-1,5-diaminopentane, 3-amino-1-propanol, 4-Amino-1-butanol, 5-amino-1-pentanol, 1-(3-aminopropyl)pyrrolidine, 4-aminophenyl disulfide and cystamine (Sunshine et al., 2012).

Example 5

Synthesis and Size Distribution of PLGA-PEI/DNA Nanoparticles

The preparation of PLGA-PEI/DNA is provided. The PLGA-PEI (w/w up to 1:1) is water soluble. Mixing of PLGA-PEI and plasmid DNA in plain medium or water results in the formation of nanoparticle or polyplex. For nanoparticles formed with PLGA-PEI (0.5:1 w/w) and DNA, the effective diameters of the nanoparticles range from 100 nm to 130 nm depending on the ratios of PLGA-PEI to DNA (Table 4). A representative size distribution for 25 µg PLGA-PEI/10 µg DNA is shown in FIG. 2. Polydispersity is between 0.1 and 0.3. The zeta potential of PEI only is up to 90 mV, but decrease to 60 mV if complexed with DNA. The sharp peak indicates the particle with uniform size around 110 nm.

Figure 3A:
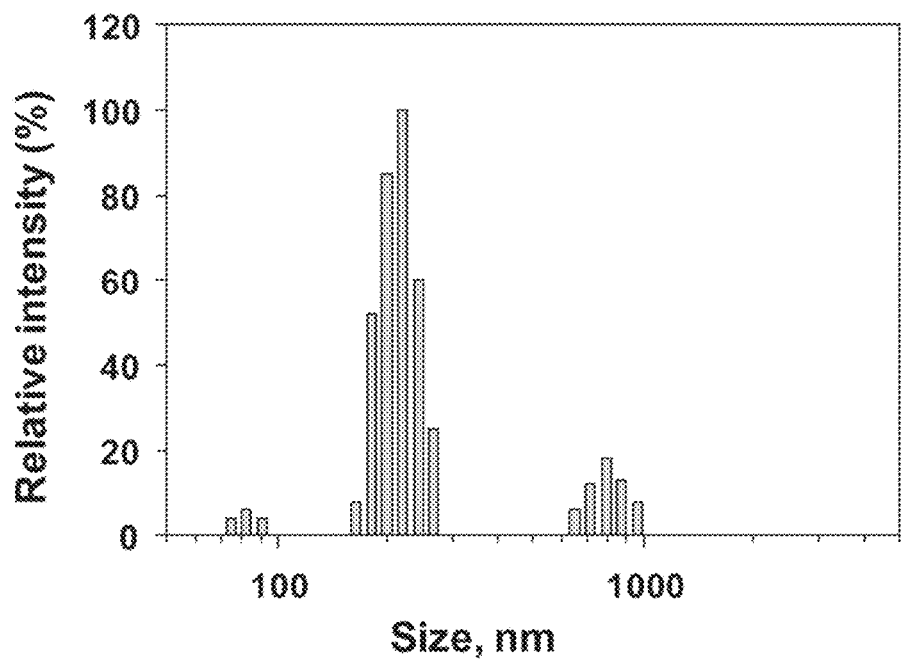
FIGS. 3A and 3B. 3A shows size distribution of PLGA/PEI/DNA primer (10 μg, 23 nucleotides, single strand).
Figure 3B:
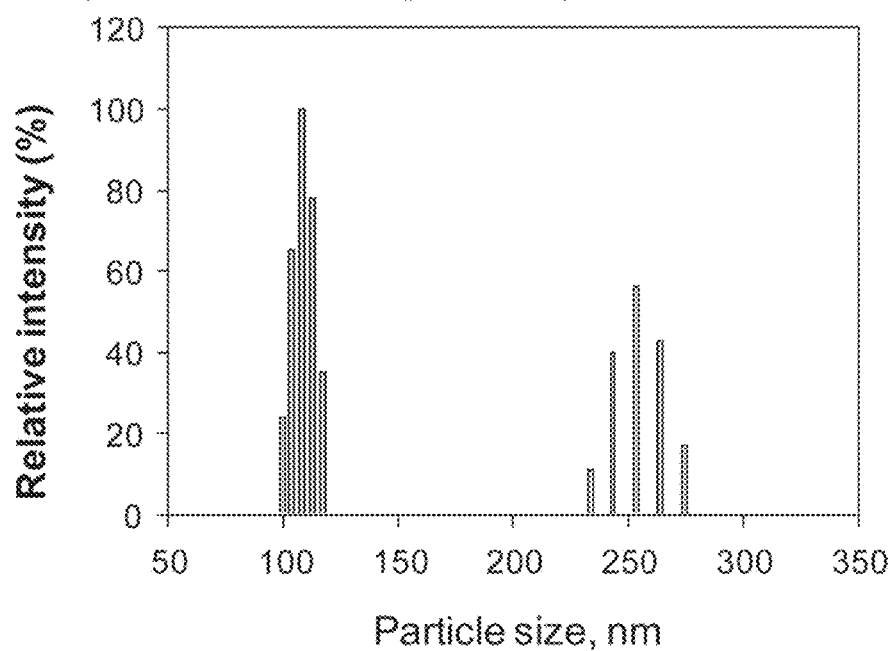

In addition to plasmid DNA delivery, the PLGA-PEI delivery system is useful for delivery oligonucleotide DNA or RNA (single stranded or double stranded) for therapeutic purposes. To characterize this, PLGA-PEI was formatted with different amounts of single stranded oligo DNA primer (23 bases) and tested size distribution. PLGA-PEI (25 µg) to 5 µg oligo DNA did not form nanoparticles; while PLGA-PEI (25 µg) to 10 µg oligo DNA formed larger particles (more 250 nm, less 900 nm) (FIG. 3A); and PLGA-PEI (25 µg) to 15 oligo DNA formed smaller particles (more 100 nm, less 250 nm) (FIG. 3B). On the other hand, PLGA-PEI (25 µg) to 20~35 µg double stranded oligo DNA formed nanoparticles (~500 nm).

The 1-(3-aminopropyl)-4-methylpiperazine modified PLGA-PEI copolymer (APMP-PLGA-PEI) is prepared directly conjugated APMP to PEI through a linker and then reacts with PLGA. Particle size distribution and zeta potential of APMP modified PLGA-PEI/DNA are listed in Table 5. For example, 15, 20, 25, 30 or 35 µg APMP-PLGA-PEI loading 10 µg plasmid DNA can form nanoparticles in the size ranging from 118 to 140 nm.

Example 6

DNA Loading Efficiency of PLGA-PEI by Optical Measurement and DNA Retardation by PLGA-PEI DNA loading efficiency of the nanoparticles was measured by spectrophotometry and gel electrophoresis. Nanoparticles were prepared with 10 µg plasmid DNA in 50 µl of water and 0 to 30 µg of PLGA-PEI in 50 µl water and made a total 100 µl solution. These nanoparticle dispersions were kept at room temperature for 30 min before use. 50 µl of each dispersion was aliquoted and centrifuged at 15 krpm (Eppendorf, centrifuge 5424) for 10 min. The absorption at 260 nm for supernatant was measured by an Agilent 8453 spectrophotometer. The gel electrophoresis was performed on 0.8% agarose gels containing 25 nM ethidium bromide. Each lane was loaded with 10 µl of the above particle solution mixed with 5 µl negatively charged dye. The gels were running at 80 mV for 45 min and imaged on a VersaDoc Imaging System with a software "Quantity One 4.6.7", Bio-RAD, USA.

Figure 4A:
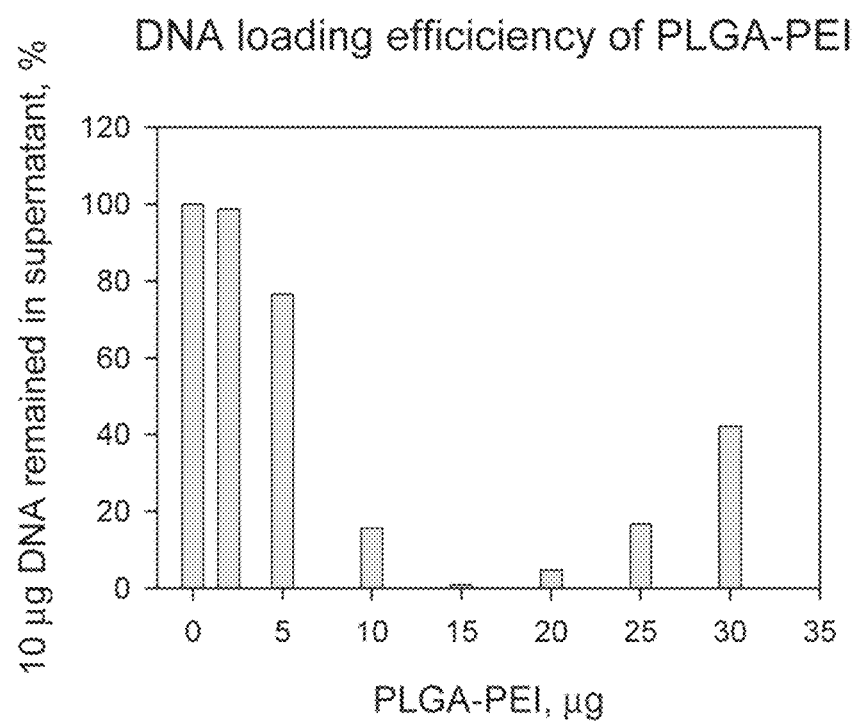
FIGS. 4A-4C.
Figure 4B:
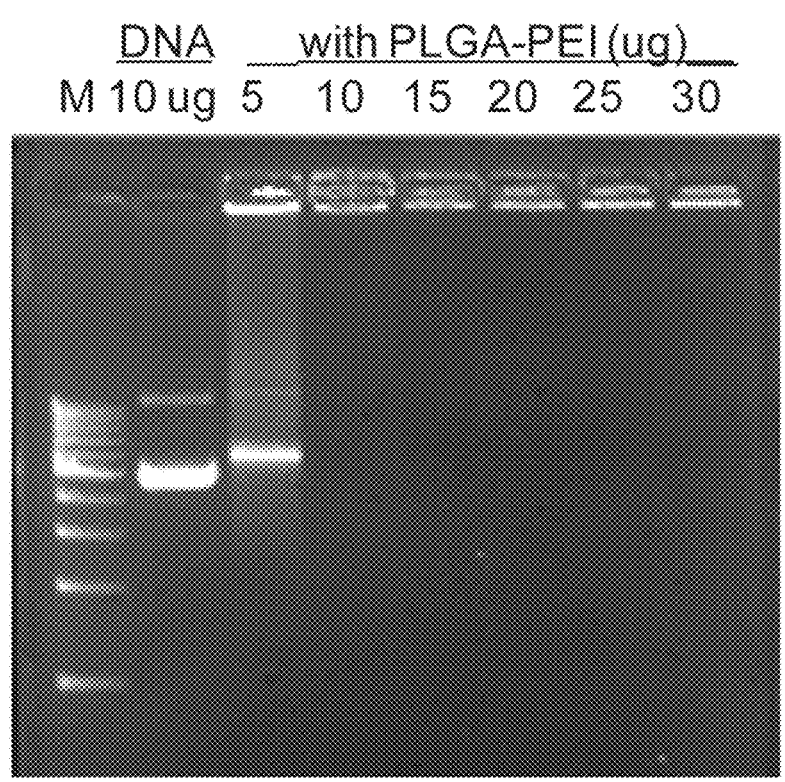
Figure 4C:
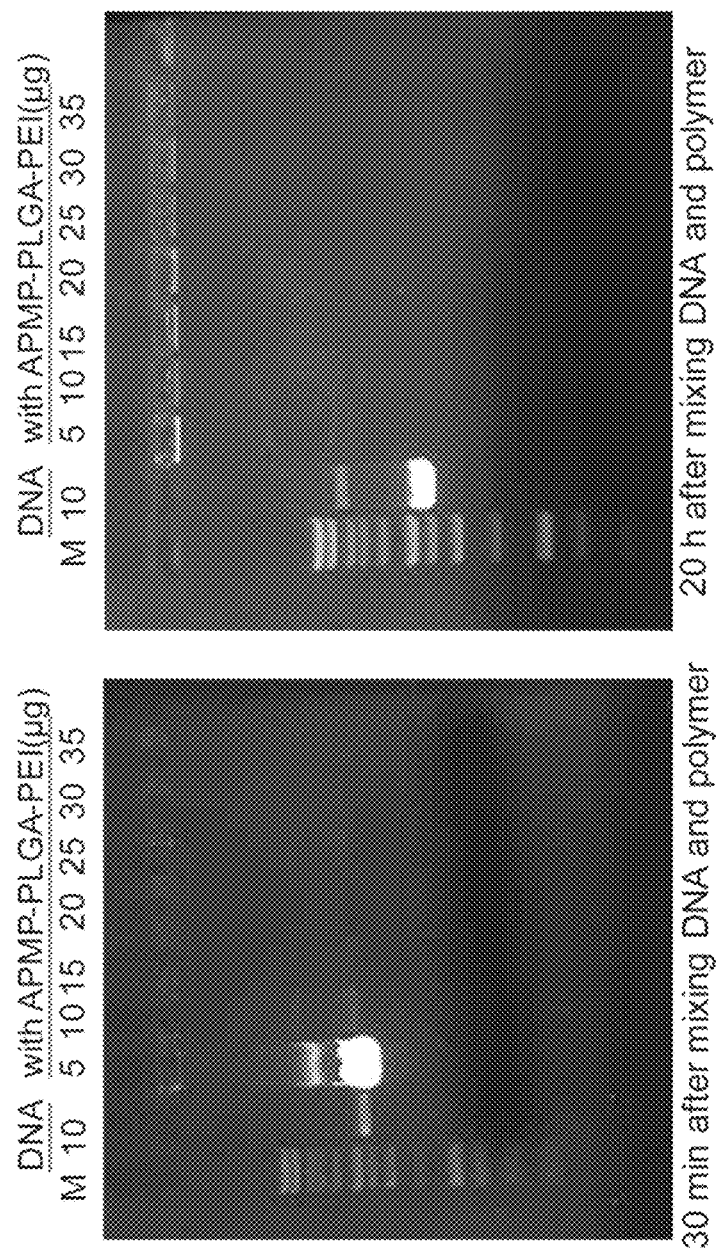

Optical measurement can determine free DNA or polymer/DNA nanoparticles suspended in the solution (FIG. 4A). It shows that for 10 µg DNA with 0 to 30 µg PLGA-PEI, DNA in the solution decreases from 100 to zero as polymer increased to 15 µg, and then increases when polymer concentration increases. This indicates that the negatively charged DNA molecules are neutralized by positive charged polymers and particles are formed and centrifuged, however, with more polymer, the polyplexes have extra charges that make the particles soluble in the aqueous solution. It does not mean that the DNA is free in the solution. As one can see from the gel electrophoresis, at a 0.5:1 (w/w) ratio, PLGA can retain most of the DNA, but it is able to retain the DNA completely at a low 1:1 (w/w) ratio, FIG. 4B. Therefore, at this ratio, the DNA loading is 100%. With more PLGA-PEI, more cationically charged polymers will bind the DNA and make it condensed. Thus, with DNA 10 µg+15 µg PLGA-PEI or above, all materials efficiently form nanoparticles with variable size and water solubility.

Example 7

Direct Observation of PLGA-PEI/DNA Nanoparticles

Figure 5A:
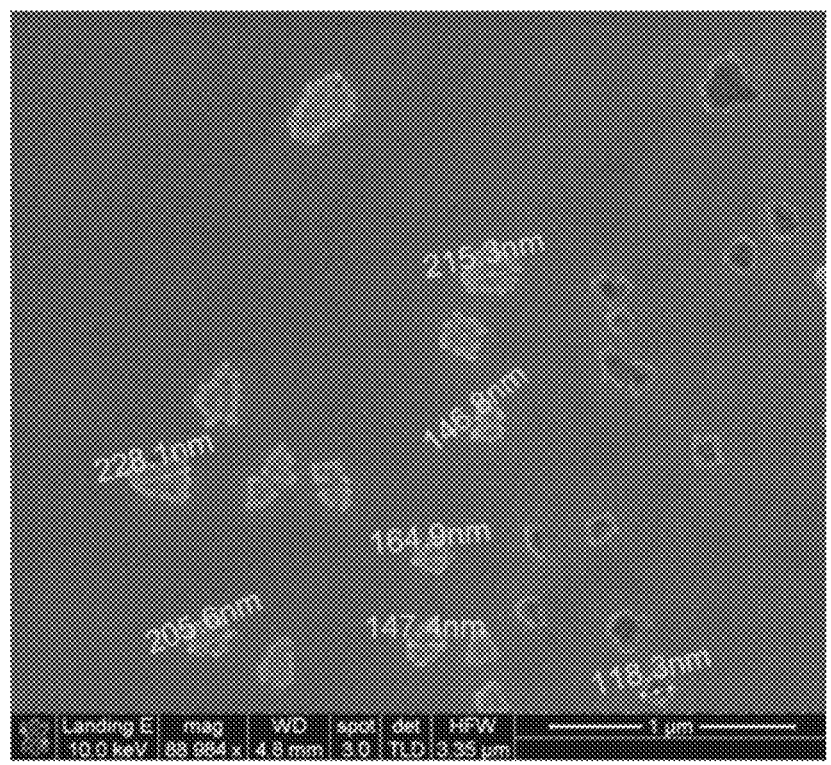
FIG. 5A-5C illustrate exemplary nanoparticle sizes.
Figure 5B:
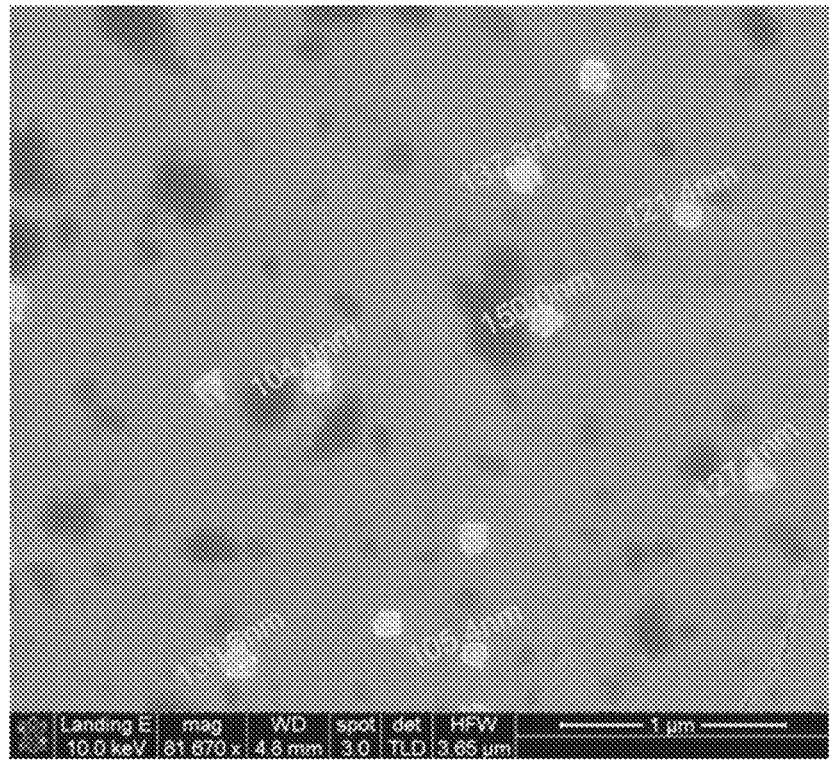
Figure 5C:
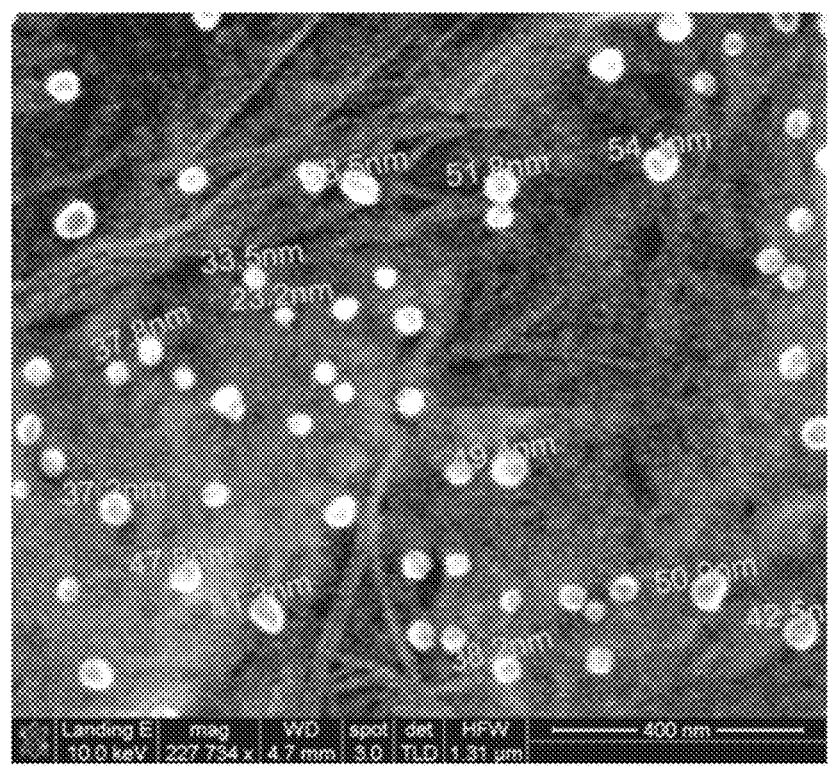

The particle image was measured with scanning electrical microscopy (SEM). Samples prepared with PLGA-PEI (64% PEI) and green fluorescence protein plasmid DNA (4.7 kbp) in nitrogen/phosphorus (N/P) ratios of 7.4, 12.3 and 17.2. When DNA is condensed with PLGA-PEI at N/P of 7.4, it is clearly showed that the DNA is wrapped by polymers although the DNA still shaped, resulted in a particle size around 150 to 230 nm (FIG. 5A). With more PLGA-PEI, however, the particles looks more solid and rigid and size decreased to 100~150 nm as N/P increased to 12.2 (FIG. 5B). When the N/P is increased to 17.2, the particles become spherical and size is down to around 50 nm (FIG. 5C). Thus, PLGA-PEI is a polymer that condenses the DNA effectively as well as controls the particle size. More polymer generates smaller size of nanoparticles. Particle size is one of important parameters of the delivery system. Different applications require particular sizes of nanoparticles for the delivery. The current invention can easily control the size of the PLGA-PEI nanoparticles.

Example 8

Cytotoxicity of PLGA-PEI/DNA Nanoparticles In Vitro

The cytotoxicity of PLGA-PEI/DNA nanoparticles and PEI/DNA complexes was investigated in human pancreatic cancer cell line (PANC-1 cells). The cells were treated overnight with nanoparticles in 10% FBS DMEM medium, then the medium was removed and cells were treated with MTT (1 mg/ml in 2% FBS medium) for 2 h before the addition of 100 µl SDS/DMF. The plates were incubated at 37 C overnight and concentration determined by optical density at 570 nm. The MTT assay is a colorimetric assay for measuring the activity of cellular enzymes that reduce the tetrazolium dye, MTT, to its insoluble formazan, giving a purple color. This assay measures the number of viable cells present.

Figure 6:
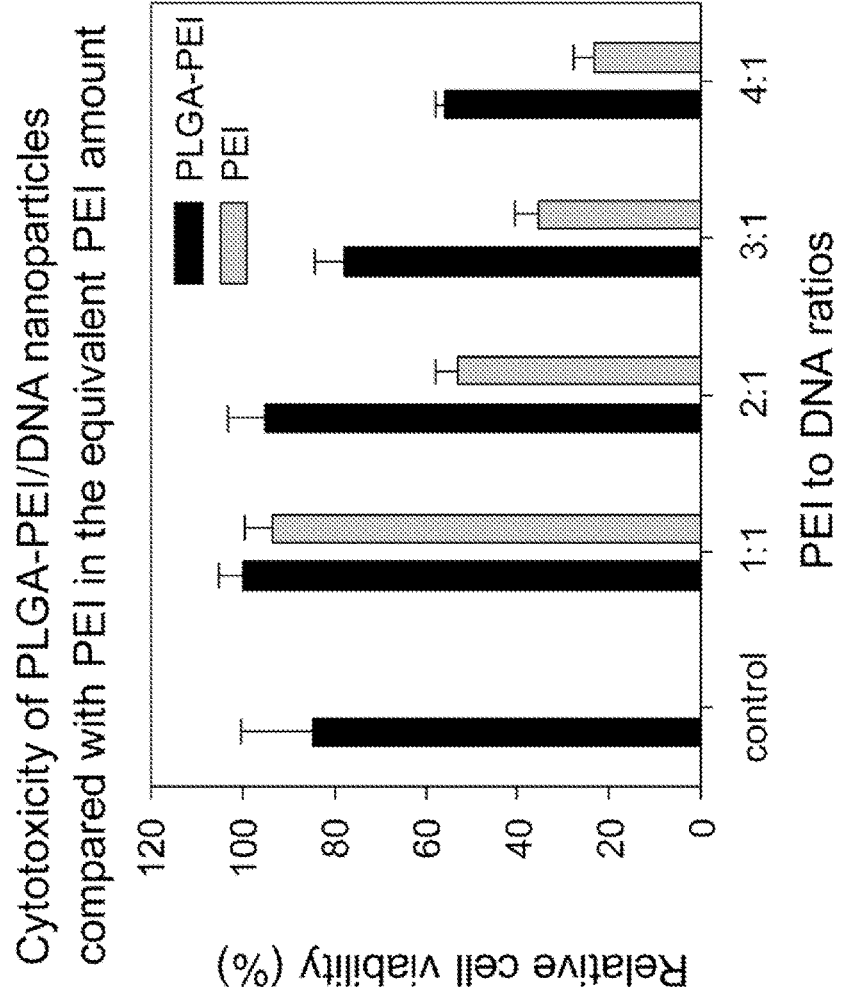
FIG. 6 shows cytotoxicity of PLGA-PEI/DNA nanoparticles compared with PEI in the equivalent PEI amount. Thus, PLGA-PEI/DNA nanoparticles have less toxicity than PEI/DNA delivery system.

Plasmid DNA amount was fixed at 1 µg/well and the same PEI to DNA ratios (i.e., the same N/P ratio) were used for different polymers to DNA as compared with PLGA-PEI (FIG. 6). The ratios of PEI to DNA ranging from 1:1 to 4:1 were studied. The MTT test results indicate that PLGA-PEI/DNA complexes have no or minor toxicity at PEI to DNA ratio up to 3:1 when compared to untreated cells. Using PEI/DNA complexes, however, approximately half of cell viability was lost when PEI to DNA ratio is 2:1. Thus, PLGA component of PLGA-PEI/DNA nanoparticles has a protective effect for PEI-induced cytotoxicity. Thus PLGA-PEI/DNA delivery system is less toxic than the PEI/DNA delivery system at the same PEI and DNA contents and conditions.

Example 9

Transfection Efficiency of PLGA-PEI/DNA (EGFP) Nanoparticles in Vitro

Figure 7A:
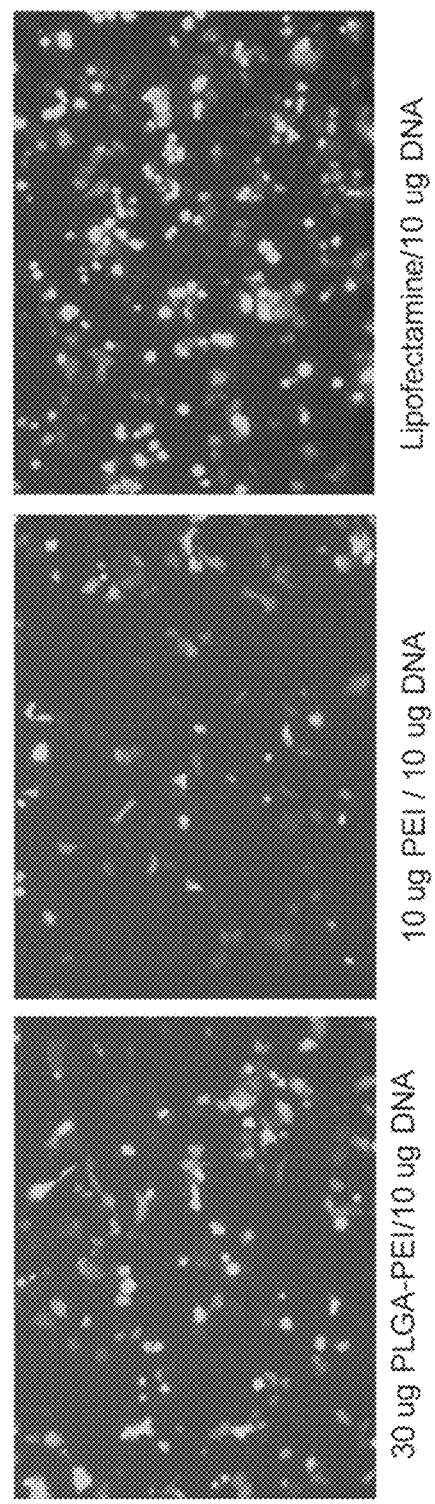
FIGS. 7A-7C.

Pancreatic cancer cell line PANC-1 cells were cultured in the presence of 10% of serum. The cells were treated overnight with nanoparticles in 10% FBS DMEM medium, then the medium was replaced with fresh medium and incubated another day. PLGA-PEI complexed with plasmid DNA encoding for green fluorescent protein (GFP) nanoparticles were evaluated for their transfection efficacy in PANC-1 cells in the presence of 10% of FBS and compared with that of Lipofectamine/DNA and PEI/DNA delivery system (FIG. 7A). PLGA-PEI/DNA nanoparticles have a better transfection activity than PEI/DNA polyplexes and similar to that of Lipofectamine/DNA in PANC-1 cells. Moreover, GFP expression in the cells with PLGA-PEI/DNA can last longer than that in those cells with PEI/DNA or lipofectamine/DNA.

Figure 7B:
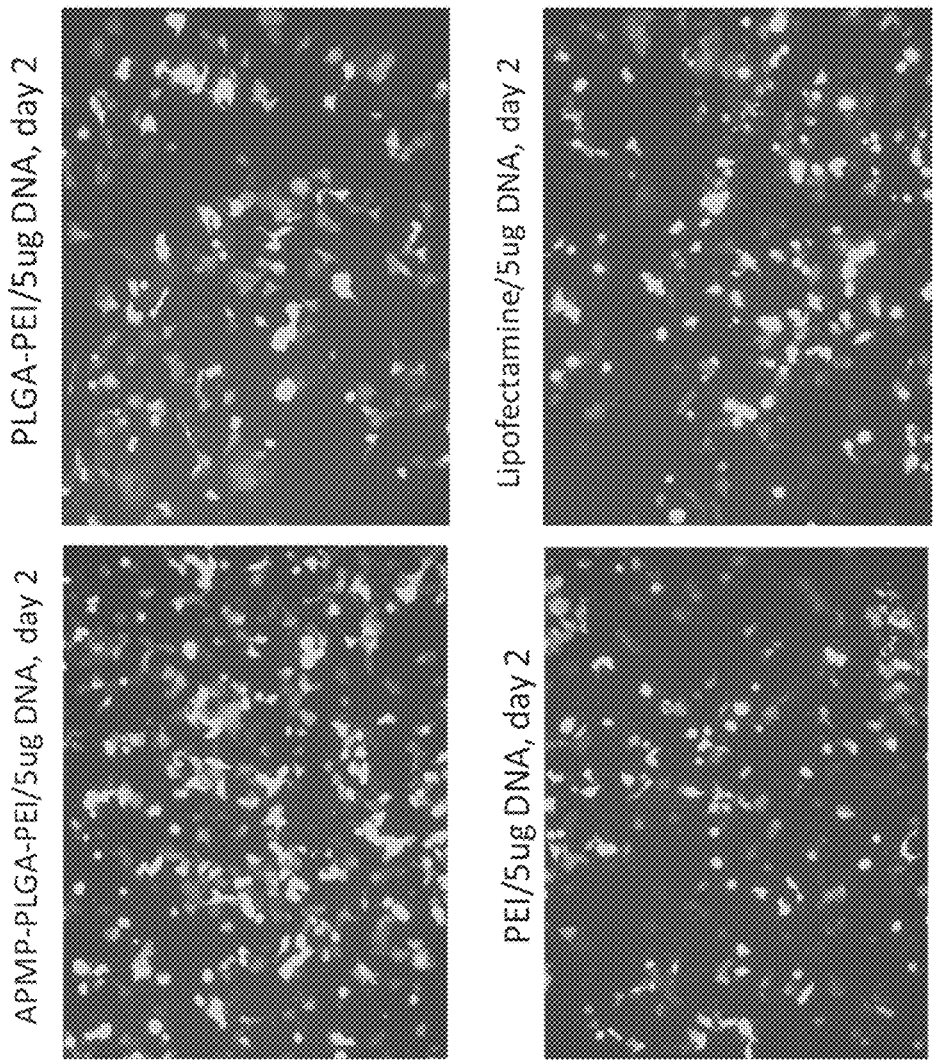

APMP (1-(3-aminopropyl)-4-methylpiperazine) was used to covalently link to PLGA and formulate APMP-PLGA-PEI. This new material is effective to load DNA and form nanoparticles (Table 5, FIG. 4B). This new material was tested in the nanoparticle formation and GFP plasmid delivery into pancreatic cancer cells (PANC-1) (FIG. 7B), and compared with Lipofectamine 2000, PEI, PLGA-PEI at the same condition (5 µg plasmid-GFP DNA). Clearly, APMP-PLGA-PEI/GFP plasmid DNA is more efficient than PLGA-PEI, PEI and lipofectamine 2000 delivery systems.

Figure 7C:
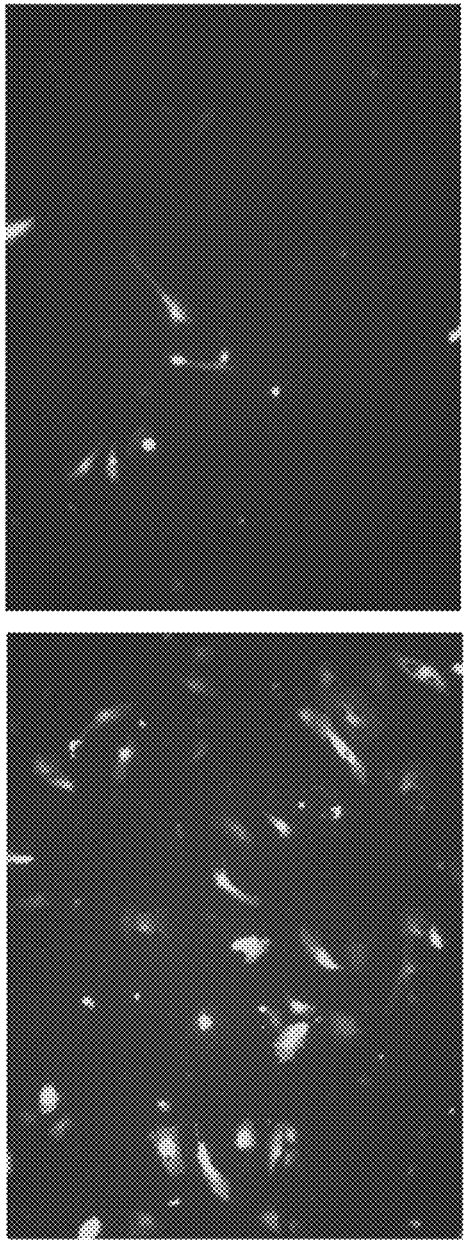

Different types of cells have different transfection rates in response to different transfection reagents. It is well known that Lipofectamine 2000 is not efficient to deliver gene to human umbilical vein endothelial cells (HUVECs) (about 2%). Gene delivery efficiency of PLGA-PEI/plasmid DNA nanoparticles in HUVEC cells was studied and compared with Lipofectamine 2000 at the same condition. HUVEVs were cultured in 10% FBS endothelial cell culture medium (EBM-2 with supplements, Lonza). The cells were treated by PLGA-PEI/plasmid DNA (25 µg PLGA-PEI/10 µg plasmid DNA containing GFP gene) or Lipofectamine 2000/10 µg DNA for overnight; and the cells were cultured with the fresh medium for another day. Fluorescence image was taken to indicate transfection rate and expression of GFP protein. PLGA-PEI nanoparticles have much higher transfection rate than Lipofectamine 2000 in HUVECs (FIG. 7C). As a new drug delivery system, PLGA-PEI nanoparticles are efficient to deliver genes or drugs to difficult-to-transfect cells such as HUVECs by other delivery systems. Thus, PLGA-PEI delivery system has significant advantages over other delivery systems such as Lipofectamine 2000.

Example 10

PLGA-PEI/DNA Nanoparticle: Toxicity Studies in Mice

Lipofectamine 2000 is not recommended to use in vivo because its toxicity for red blood cells and other cells. Only some liposome formulations and PEI can be used in vivo; but their toxicity is well known. In vivo toxicity of PLGA-PEI/DNA was compared with PEI/DNA. For PEI/DNA delivery system, all mice (n=3) died after tail vein injected with 50 µg DNA complexed with PEI (75 µg) at a w/w ratio of 1.5:1; while all mice (n=3) survived after tail vein injection with 50 µg DNA complexed with PLAE-PEI (125 µg). Furthermore, all mice (n=8) received 100 µg DNA with PLGA-PEI (250 µg) survived. Mice (n=4) received 200 µg DNA with PLGA-PEI (500 µg) survived 50%. Thus, PLGA-PEI/DNA shows much less in vivo toxicity than PEI/DNA. PLGA significantly reduces PEI-associated toxicity in vivo. It is one of major advantages of current invention for in vitro and in vivo applications of gene or drug delivery.

Example 11

Figure 8:
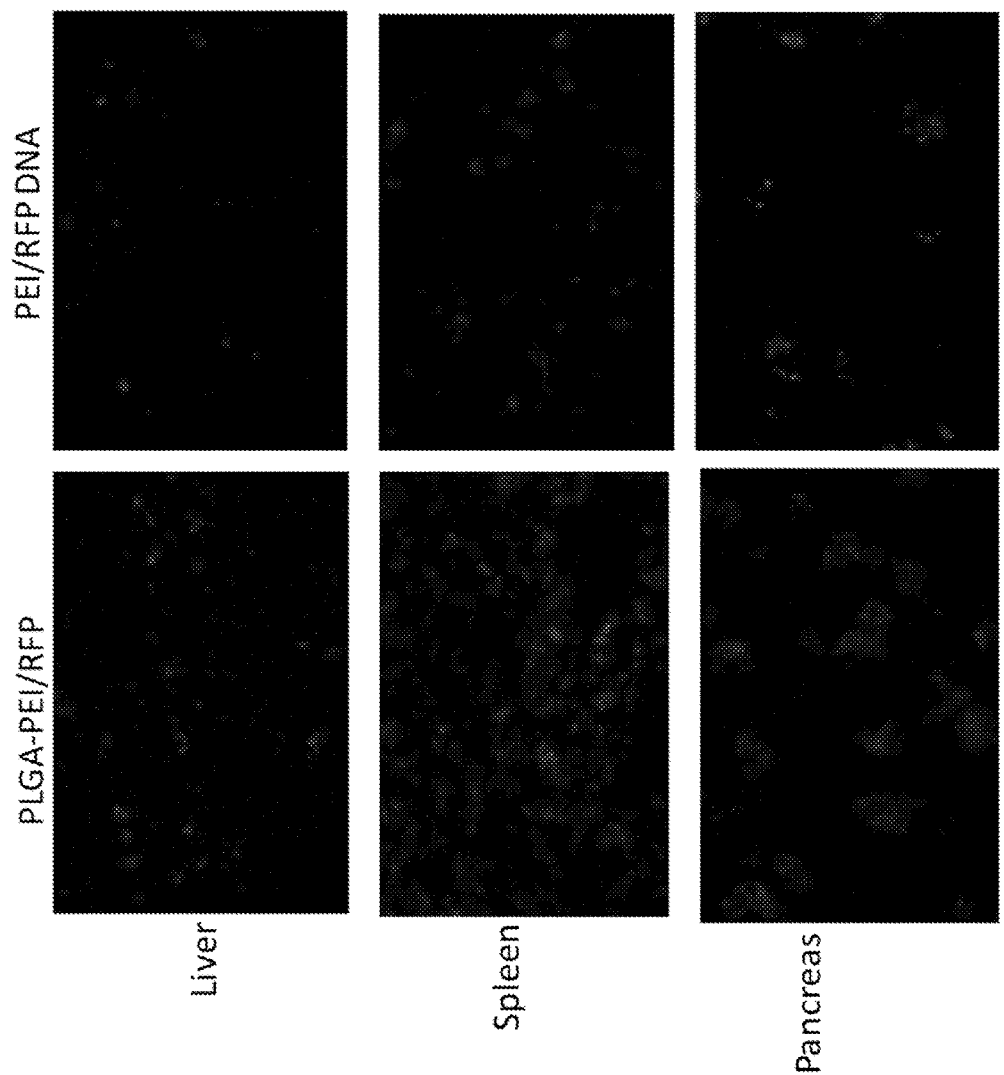
FIG. 8 shows PLGA-PEI/red fluorescence protein (RFP) DNA-treated mice and those treated with PEI/DNA controls, specifically for the liver, spleen, and pancreas. PLGA-PEI nanoparticle delivery system is more efficient than PEI-based delivery system in vivo.

Delivery Efficiency of PLGA-PEI/Red Fluorescence Protein (RFP) DNA Nanoparticles in the Mouse Model Using PLGA-PEI as a delivery system to deliver red fluorescence protein (RFP) plasmid DNA to white mice by tail vein injection to study the DNA transfection in mouse organs and compared with PEI/DNA delivery. Three doses of 30 µg DNA with either PLGA-PEI or PEI were injected to mice in 5 days, then the mice were sacrificed in day 7 and organ tissues were checked by red fluorescence for the DNA transfection. For PLGA-PEI/DNA treated mice, organs such as liver, spleen and pancreas showed strong red fluorescence; PEI/DNA treated mice showed only weak red fluorescence in liver, spleen and pancreas (FIG. 8). Thus, PLGA-PEI delivery system is much more efficient than PEI-based delivery system in vivo.

Figure 9:
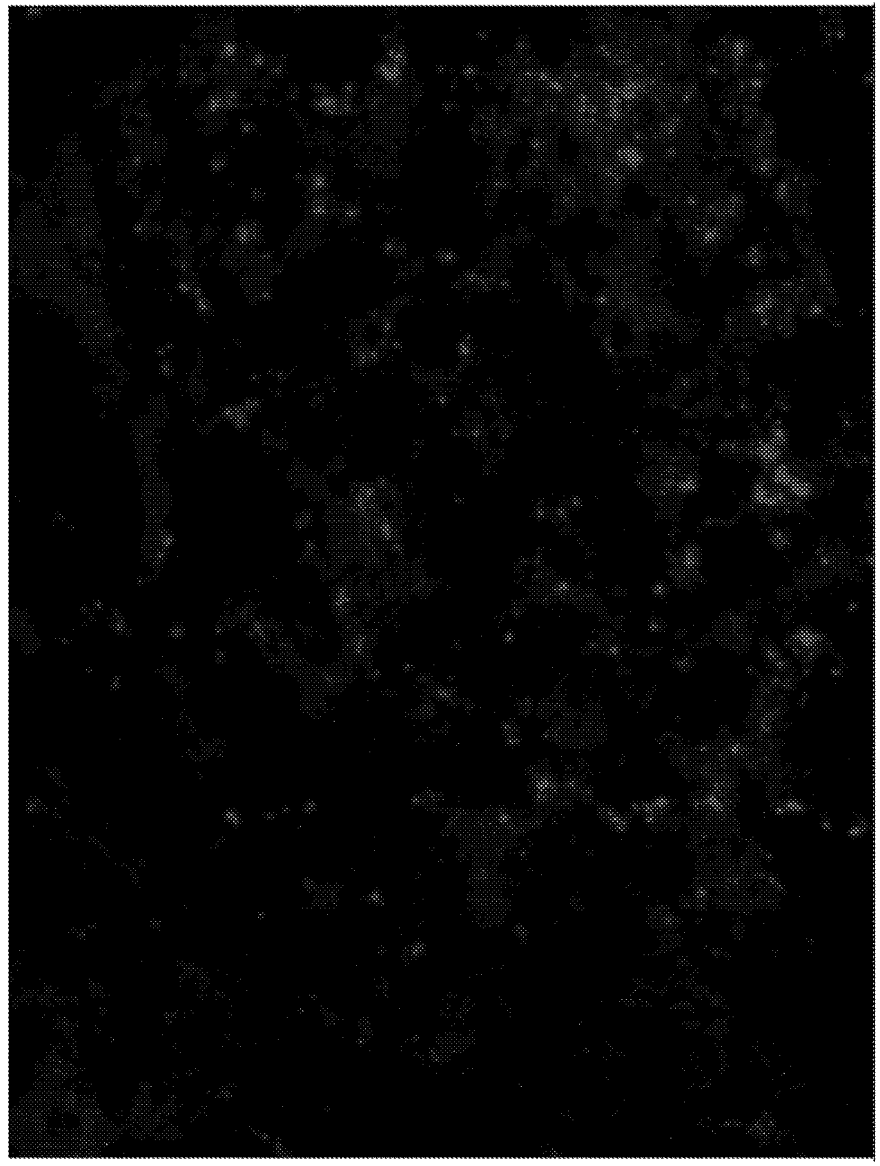
FIG. 9 demonstrates PLGA-PEI delivery of 10 μg RFP DNA and analysis of the tumor three days later. The PLGA-PEI nanoparticle is effective to deliver DNA into the tumor in the mouse model.

Furthermore, PLGA-PEI/DNA system was tested in pancreatic tumors (as an example) in a nude mouse model. Nude mice were injected subcutaneously with another human pancreatic cancer cell line (AsPC-1 cells), tumors were grown up in two weeks. They used 25 µg PLGA-PEI and delivered 10 µg RFP NDA via direct injection to the tumor. Three days later, the tumor was taken out and strong red fluorescence was found in the tumor, indicating high DNA transfection efficacy inside the tumor tissue (FIG. 9).

Example 12

Figure 10A:
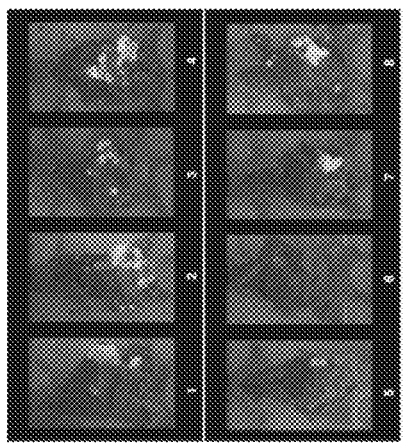
FIGS. 10A and 10B demonstrate the therapeutic application of intravenous administration of PLGA-PEI/miR-198 nanoparticles for the treatment of pancreatic cancer in a mouse model. Intravenous (IV) delivery of miR-198 loaded PLGA-PEI nanoparticles reduces tumor burden and metastatic spread in the mouse model by both fluorescence imaging analysis (FIG. 10A) and direct measurement of dissected tumors (FIG. 10B).
Figure 10B:
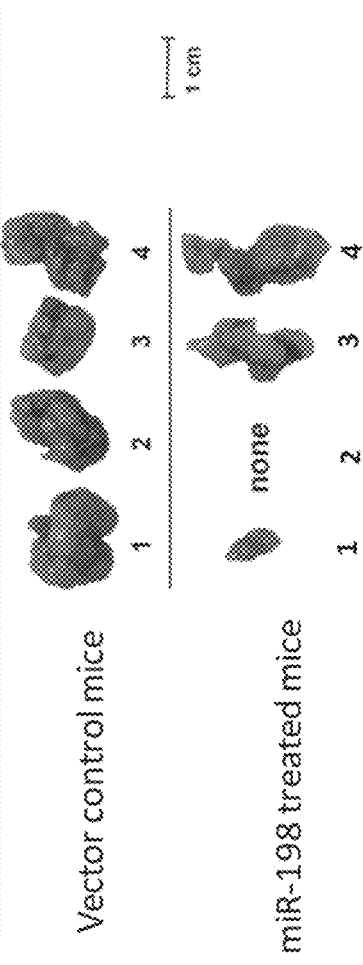

Intravenous (IV) Delivery of MIR-198 Loaded PLGA-PEI Nanoparticles Reduces Tumor Burden and Metastatic Spread in an Orthotopic Pancreatic Cancer Model Previous studies demonstrated mesothelin (MSLN) overexpression and miR-198 downregulation lead to increased migration and invasion of pancreatic cancer (PC) cells in vitro and increased tumor spread in vivo; and miR-198 reconstitution can reduce metastatic spread as well as tumor volume. It was considered whether therapeutic delivery of miR-198 by PLGA-PEI nanoparticles could reduce the metastatic spread of MSLN-overexpressing PC cells in an orthotopic PC tumor model. Nude mice were implanted with pancreatic cancer cell (Mia-MSLN) for two weeks, and assigned two groups. The control mice received PLGA-PEI/empty vector plasmid (50 µg) via tail vein injection 3 times/week for 3 weeks; and the treated mice received PLGA-PEI/miR-198 plasmid (50 µg) via tail vein injection 3 times/week for 3 weeks. All animals were sacrificed at 6 weeks. Tumor size and metastasis of the mice were observed under fluorescence imaging (FIG. 10A) and surgical dissection (FIG. 10B). Data showed that intravenous (IV) delivery of miR-198 loaded PLGA-PEI nanoparticles significantly reduces tumor burden and metastatic spread in an orthotopic pancreatic cancer model.

Example 13

Figure 11A:
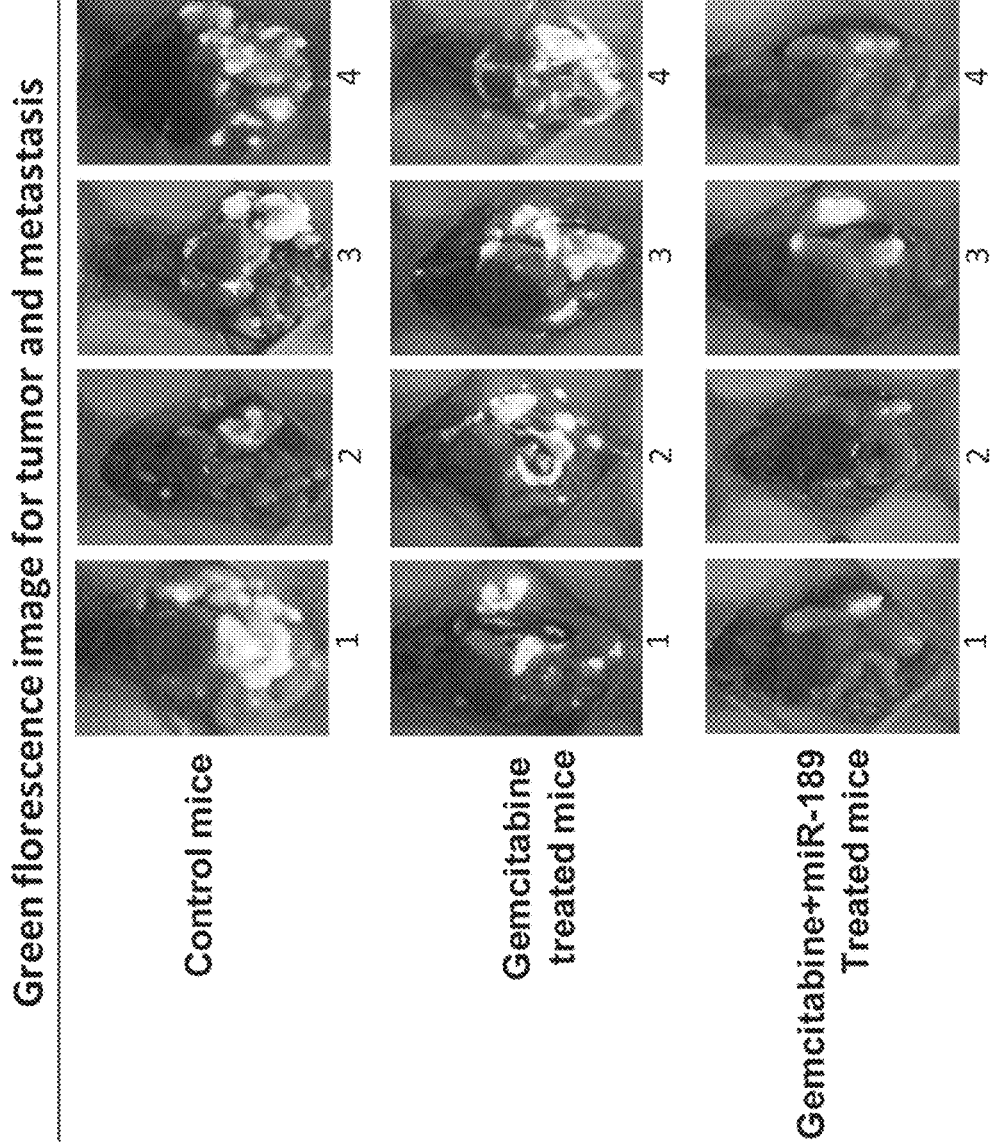
FIGS. 11A and 11B shows that the therapeutic application of intraperitoneal (IP) administration of PLGA-PEI/miR- 198 nanoparticles in the combination of chemotherapy Gemcitabine for the treatment of pancreatic cancer in a mouse model.
Figure 11B:
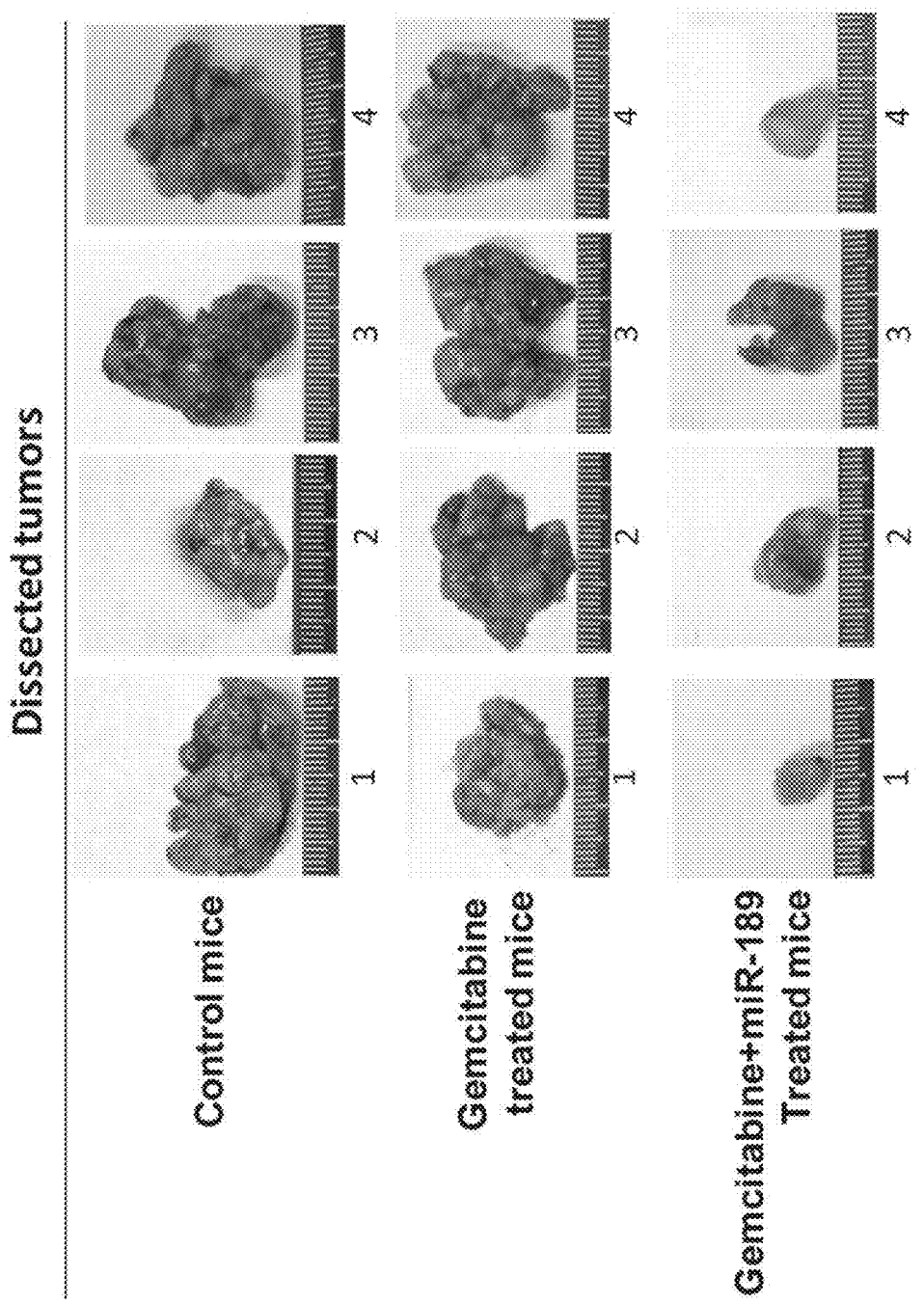
Figure 12A:
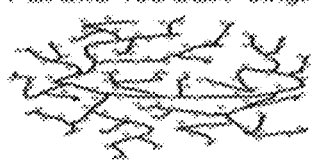
FIGS. 12A-12C. Chemical structure modeling and nanoparticle formation of PLGA-PEI copolymer and plasmid DNA.
Figure 12B:
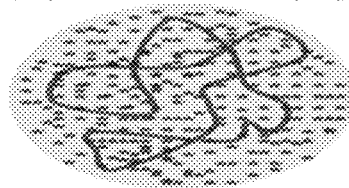
Figure 12C:
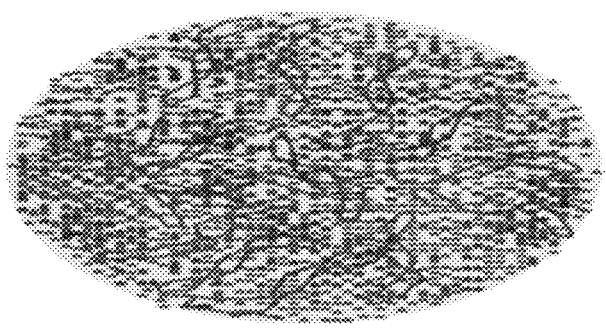

Intraperitoneal (IP) Delivery of MIR-198 Loaded PLGA-PEI Nanoparticles and Gemcitabine Synergistically Reduces Tumor Burden and Metastatic Spread in an Orthotopic Pancreatic Cancer Model Orthotopic tumors were implanted by injecting 3×10$^6$ pancreatic cell line (MIA-MSLN-GFP cells) directly into the pancreas. Two weeks after tumor cell implantation, therapy was carried out in 3 groups (4 mice/group). Control mice did not receive any treatment. Gemcitabine mice received with clinical chemotherapy agent Gemcitabine (50 mg/kg body weight) via intraperitoneal injection 3 time a week for 3 weeks. Gemicitabine+miR-198 mice received combination of gemicitabine (50 mg/kg body weight) and PLGA-PEI/miR-198 plasmid (50 mg) via intraperitoneal injection 3 time a week for 3 weeks. All animals were sacrificed at 6 weeks. Tumor size and metastasis of the mice were observed under fluorescence imaging (FIG. 11A) and surgical dissection (FIG. 11B). This data demonstrated that the combination therapy with Gemcitabine and PLGA-PEI nanoparticle encapsulated miR-198 effectively reduces pancreatic cancer growth and metastasis in the orthotopic PC mouse model.

Example 14

Therapeutic XIST Fragment and PLGA-PEI-Based Delivery System for the Treatment of Pancreatic Cancer Pancreatic cancer (PC) is the fourth leading cause of cancer mortality in the United States. Estimates indicate that in 2014 about 46,420 new cases will be diagnosed and 39,590 people will die of PC. Most patients are diagnosed with late stage PC and are not eligible for surgical resection. The mortality rate of PC patients has not improved significantly in the past two decades; the five-year survival rate for PC still remains less than 5%. Effective therapy for PC is urgently needed. The initiation and progression of PC involve a step-wise accumulation of genetic alterations, such as point mutations, chromosome translocations, and changes in gene copy number that lead to the inactivation of tumor suppressor genes and the activation of oncogenes.

The human X chromosome carries approximately 1,500 genes, some of which represent potential sites for the genetic alterations that are observed in human cancers of the breast, ovary, prostate, testicle, lung, liver, colon, skin, kidney, and other organs. In females, one copy of the X chromosome is normally inactivated by several mechanisms, which include DNA methylation and hypoacetylation, and a unique function of XIST (X-inactive-specific transcript) RNA, a 17 kb spliced and polyadenylated RNA with no coding capacity. XIST RNA remains confined to the nucleus, where it spreads in cis on the inactivated X chromosome. In females, several splicing isoforms of XIST RNA have been discovered, including AK054860 (2.659 kb, a part of exon 6), AK025198 (2.176 kb), and X56199 (1.614 kb). In males, XIST is not expressed, except in the germ cells of the testis. The loss of XIST has been observed in some breast, ovarian, and cervical cancers in females, and it seems to be associated with a poor cancer prognosis.

Figure 13A:
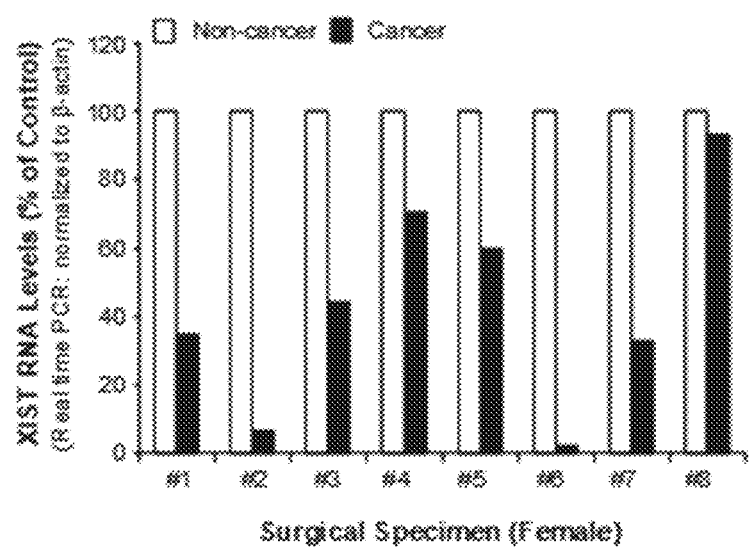
FIGS. 13A and 13B shows expression of XIST in female pancreatic cancer tissues and cell lines according to real time PCR analysis.
Figure 13B:
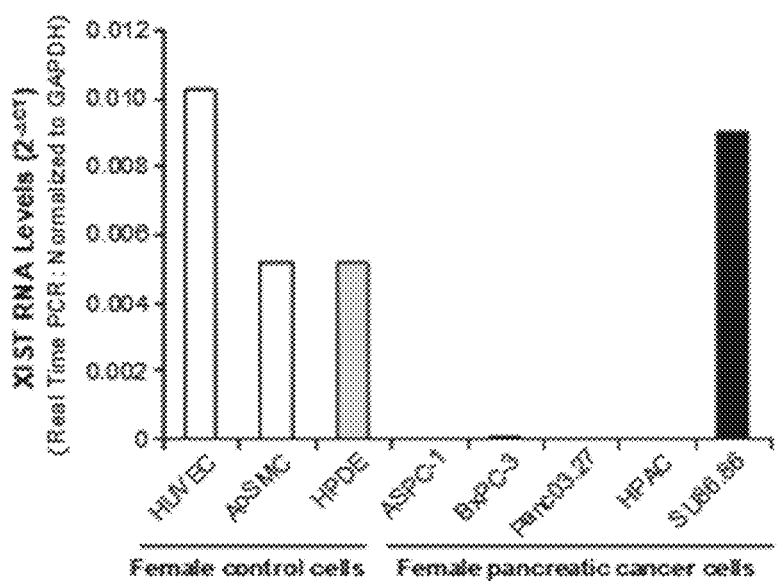
Figure 15A:
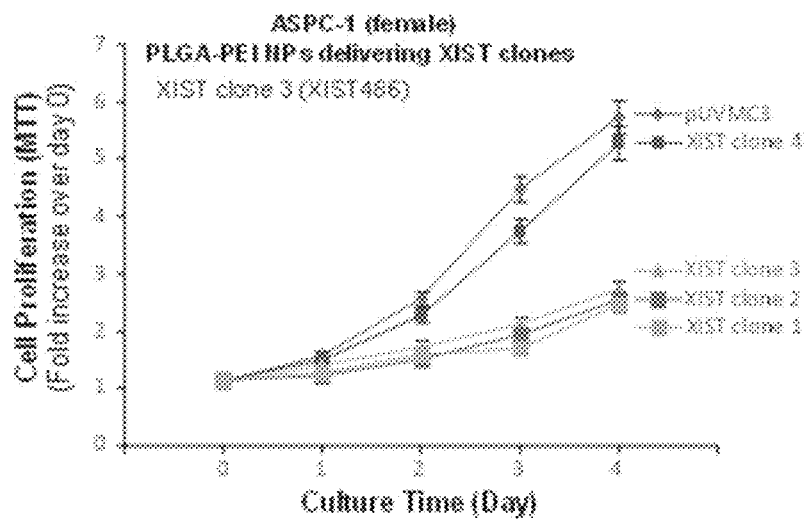
FIGS. 15A and 15B shows serial XIST truncation mutant cloning and functional analysis (MTT). Original XIST isoform clone (AK054860, 2.659 kb, clone 1) was subcloned into three shortened segments (clones 2, 3, and 4) in clinically-approved plasmid vector pUVMC3. Each clone was transfected into ASPC-1 (female) (FIG. 15A) and PANC-1 (male) (FIG. 15B) cell lines, with PLGA-PEI nanoparticles. MTT was assayed at 0, 1, 2, 3, and 4 days. XIST clone 3 (XIST486) is the shortest functional domain.
Figure 15B:
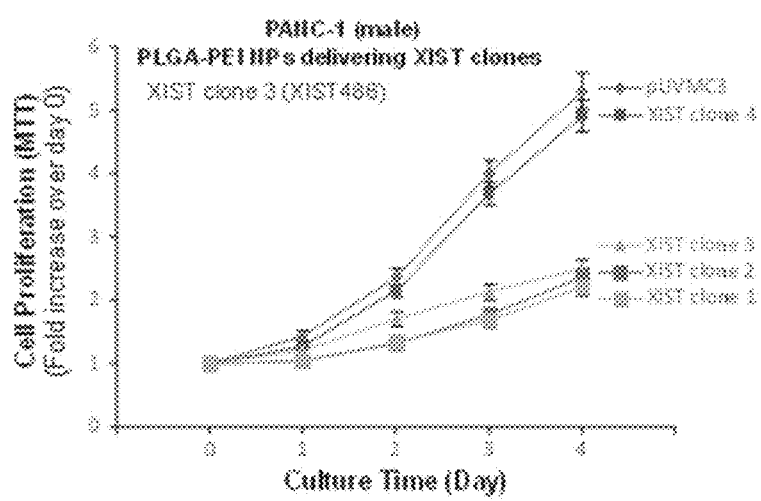

There are new discoveries in the area of XIST, which is substantially downregulated in most female human PC tissues and cancer cell lines (FIGS. 13A and 13B). More importantly, the functional significance is discovered of the loss of XIST RNA expression in these female cells by imposing forced expression of XIST RNA. Gene delivery of XIST RNA into female PC cell lines (in which XIST was significantly downregulated) resulted in the inhibition of in vitro cell proliferation and in the reduction in tumor growth in xenografted mouse models (FIGS. 14A-14D). Surprisingly, forced expression of a XIST fragment (AK054860, 2.659 kb, a part of exon 6) in the male human PC cell line PANC-1 (which does not express XIST) also significantly reduced cell proliferation (MTT test), migration (Boyden chamber assay) in vitro, and inhibited tumor growth in nude mouse models (n=8, p<0.05). A XIST gene fragment (AK054860, 2.659 kb, a part of exon 6) was subcloned into plasmid pUMVC3 vector, which is an approved vector for clinical trials. Furthermore, a short function domain (486 bps) is identified of the XIST gene fragment with serial truncation subcloning experiments and with a cell proliferation assay (MTT test) using the PLGA-PEI NP delivery system in both female and male PC cell lines (ASPC-1 and PANC-1, respectively) (FIGS. 15A and 15B).

REFERENCES

All patents and publications mentioned in the specification are indicative of the level of those skilled in the art to which the invention pertains. All patents and publications are herein incorporated by reference in their entirety to the same extent as if each individual publication was specifically and individually indicated to be incorporated by reference.

Akinc A, Thomas M, Klibanov A M, Langer R. Exploring polyethyleniminemediated DNA transfection and the proton sponge hypothesis. J Gene Med 2005; 7(5):657e63.

M Arruebo, M Valladares and A Gonzalez-Fernandez, Antibody-Conjugated Nanoparticles for Biomedical Applications. Journal of Nanomaterials. 2009, 2009: 1-24.

B Arunachalam, U T Phan, H J Geuze and P Cresswell, Enzymatic reduction of disulfide bonds in lysosomes: Characterization of a Gamma-interferon-inducible lysosomal thiol reductase (GILT). PNAS, 2000 vol. 97: 2 745-750

J Y Bae, M Mie and E Kobatake, Targeted Gene Delivery via PEI Complexed with an Antibody. Appl Biochem Biotechnol, 2012, 168:2184-2190

Bhise N S, Gray R S, Sunshine J C, Htet S, Ewald A J, Green J J. The relationship between terminal functionalization and molecular weight of a gene delivery polymer and transfection efficacy in mammary epithelial 2-D cultures and 3-D organotypic cultures. Biomaterials. 2010; 31(31): 8088-8096.

Bivas-Benita, M, Lin, M Y, Bal, S M, van Meijgaarden, K E, Franken, K L, Friggen, A H, Junginger, H E, Borchard, G, Klein, M R and Ottenhoff, T H, Pulmonary delivery of DNA encoding *Mycobacterium tuberculosis* latency antigen Rv1733c associated to PLGA-PEI nanoparticles enhances T cell responses in a DNA prime/protein boost vaccination regimen in mice. Vaccine, 2009; 27: 4010-7.

Bivas-Benita, M, Romeijn, S, Junginger, H E and Borchard, G, PLGA-PEI nanoparticles for gene delivery to pulmonary epithelium. Eur J Pharm Biopharm, 2004; 58: 1-6.

Bullock, J, Chowdhury, S, Severdia, A, Sweeney, J, Johnston, D and Pachla, L, Comparison of results of various methods used to determine the extent of modification of methoxy polyethylene glycol 5000-modified bovine cupri-zinc superoxide dismutase. Anal Biochem, 1997; 254: 254-62.

D S Collins, E R Unanue and C V Harding. Reduction of disulfide bonds within lysosomes is a key step in antigen processing. The Journal of Immunology. 1991 vol. 147 no. 12 4054-4059

Eltoukhy A A, Siegwart D J, Alabi C A, Rajan J S, Langer R, Anderson D G. Effect of molecular weight of amine end-modified poly(β-amino ester)s on gene delivery efficiency and toxicity. Biomaterials. 2012 May; 33(13): 3594-603.

Forrest M L, Koerber J T, Pack D W. A degradable polyethylenimine derivative with low toxicity for highly efficient gene delivery. Bioconjugate Chem. 2003, 14 (5), 934-940.

Gargouri, M, Sapin, A, Arica-Yegin, B, Merlin, J L, Becuwe, P and Maincent, P, Photochemical internalization for pDNA transfection: evaluation of poly(d,l-lactide-co-glycolide) and poly(ethylenimine) nanoparticles. Int J Pharm, 2011; 403: 276-84.

Green J J, Zugates G T, Tedford N C, Huang Y, Griffith L G, Lauffenburger D A, Sawicki J A, Langer R, Anderson D G. Combinatorial modification of degradable polymers enables transfection of human cells comparable to adenovirus. Adv. Mater. 2007, 19(19), 2836-2842.

Hyo Jin Kang, Young Ji Kang, Young-Mi Lee, Hyun-Hee Shin, Sang J. Chung, Sebyung Kang Developing an antibody-binding protein cage as a molecular recognition drug modular nanoplatform. Biomaterials. 2012, 33, 5423-5430

Lee J S, Green J J, Love K T, Sunshine J, Langer R, Anderson D G. Gold, poly(beta amino ester) nanoparticles for small interfering RNA delivery. Nano Lett 2009; 9(6):2402-6.

Moghimi S M, Symonds P, Murray J C, Hunter A C, Debska G, Szewczyk A. A two stage poly(ethylenimine)-mediated cytotoxicity: implications for gene transfer/therapy. Mol Ther 2005; 11(6):990e5.

Nam, Y S, Kang, H S, Park, J Y, Park, T G, Han, S H and Chang, I S, New micelle-like polymer aggregates made from PEI-PLGA diblock copolymers: micellar characteristics and cellular uptake. Biomaterials, 2003; 24: 2053-9.

Shau, M D, Shih, M F, Lin, C C, Chuang, I C, Hung, W C, Hennink, W E and Cherng, J Y, A one-step process in preparation of cationic nanoparticles with poly(lactide-co-glycolide)-containing polyethylenimine gives efficient gene delivery. Eur J Pharm Sci, 2012; 46: 522-9.

Sun C, Tang T, Uludağ H, Cuervo J E. Molecular dynamics simulations of DNA/PEI complexes: Effect of PEI branching and protonation state. Biophys J. 2011 Jun. 8; 100(11): 2754-2763.

Sun C, Tang T, Uludağ H. Molecular dynamics simulations for complexation of DNA with 2 kDa PEI reveal profound effect of PEI architecture on complexation. J Phys Chem B. 2012 Mar. 1; 116(8):2405-13.

Sunshine J, Green J J, Mahon K, Yang F, Eltoukhy A, Nguyen D N, et al. Small molecule end group of linear polymer determine cell-type gene delivery efficacy. Adv Mater 2009; 21(48):4947-51.

Sunshine J C, Peng D Y, Green J J. Uptake and transfection with polymeric nanoparticles are dependent on polymer end-group structure, but largely independent of nanoparticle physical and chemical properties. Mol. Pharmaceutics, 2012, 9 (11):3375-3383.

Sunshine J C, Sunshine S B, Bhutto I, Handa J T, Green J J. Poly(β-Amino Ester)-Nanoparticle Mediated Transfection of Retinal Pigment Epithelial Cells In vitro and In vivo. PLoS ONE 2012; 7(5): e37543. doi:10.1371/journal.pone.0037543

Utsuno K, Uludag H. Thermodynamics of polyethylenimine-DNA binding and DNA condensation. Biophys J. 2010 Jul. 7; 99(1): 201-207.

von Harpe, A, Petersen, H, Li, Y and Kissel, T, Characterization of commercially available and synthesized polyethylenimines for gene delivery. J Control Release, 2000; 69: 309-22.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A composition comprising a copolymer consisting of lactide-co-glycolide and PEI, wherein single lactide-co-glycolide units are each conjugated to primary amines of PEI through an amide linkage, wherein the w/w ratio of LGA to PEI is 0.5:1 to 5:1,
wherein the composition further comprises at least one therapeutic and/or diagnostic agent and wherein the composition is in the form of a nanoparticle.

2. A copolymer composition comprising lactide-co-glycolide and PEI, wherein single lactide-co-glycolide units are each conjugated to primary amines of PEI through an amide linkage, and wherein the primary amine concentration is about 40% to about 55%.

3. The composition of claim 2, wherein the primary amine concentration is about 45% to about 55%, about 45% to about 52%, or about 46% to about 52%.

4. The composition of claim 1, wherein when the ratio of LGA to PEI is 0.5:1 w/w, and a nanoparticle loaded with at least one therapeutic and/or diagnostic agent has an effective diameter between 100 and 130 nm.

* * * * *